(12) United States Patent
Billings et al.

(10) Patent No.: US 10,600,517 B2
(45) Date of Patent: Mar. 24, 2020

(54) NETWORK SYSTEM OF INDIVIDUAL USER DEVICES TO GENERATE GROUP IMPLEMENTED TREATMENT PLAN

(71) Applicant: Medsphere Systems Corporation, Carlsbad, CA (US)

(72) Inventors: Edmund Billings, San Francisco, CA (US); Steven Marks, Vista, CA (US); Cynthia Yamaga, Oceanside, CA (US)

(73) Assignee: Medsphere Systems Corporation, Carlsbad, CA (US)

( * ) Notice: Subject to any disclaimer, the term of this patent is extended or adjusted under 35 U.S.C. 154(b) by 118 days.

(21) Appl. No.: 15/882,238

(22) Filed: Jan. 29, 2018

(65) Prior Publication Data

US 2018/0211731 A1 Jul. 26, 2018

Related U.S. Application Data

(63) Continuation-in-part of application No. 14/025,611, filed on Sep. 12, 2013, now abandoned.

(60) Provisional application No. 61/818,310, filed on May 1, 2013.

(51) Int. Cl.
*G16H 80/00* (2018.01)
*G16H 40/20* (2018.01)
*G16H 10/60* (2018.01)

(52) U.S. Cl.
CPC ............. *G16H 80/00* (2018.01); *G16H 10/60* (2018.01); *G16H 40/20* (2018.01)

(58) Field of Classification Search
CPC .............................. G16H 10/60; G16H 40/20
See application file for complete search history.

(56) References Cited

U.S. PATENT DOCUMENTS

| | | | |
|---|---|---|---|
| 6,208,974 B1 | 3/2001 | Campbell et al. |
| 7,428,494 B2 | 9/2008 | Hasan et al. |
| 8,021,147 B2 | 9/2011 | Sporbert et al. |
| 8,160,901 B2 | 4/2012 | Heywood et al. |
| 8,204,771 B1 | 6/2012 | Fackler et al. |
| 8,271,294 B2 | 9/2012 | Eisenberger et al. |
| 9,058,635 B1 | 6/2015 | Rybkin |
| 2003/0101076 A1 | 5/2003 | Zaleski |

(Continued)

FOREIGN PATENT DOCUMENTS

| EP | 1244994 A1 | 10/2002 |
|---|---|---|
| EP | 1423045 B1 | 1/2007 |

(Continued)

OTHER PUBLICATIONS

Gordon et al. Improving Reassessment and Documentation of Pain Management. Sep. 2008, vol. 34, No. 9, pp. 509-517.

(Continued)

*Primary Examiner* — John P Go
(74) *Attorney, Agent, or Firm* — Wilson Sonsini Goodrich and Rosati, P.C.

(57) ABSTRACT

A networked system of individual user devices is provided to generate a group implemented treatment plan. Updates to the treatment plan are made by the user devices receiving updates from the individual team members, the user devices sending the information to the server, the server dynamically compiling and updating the treatment plan and related information, and the server providing all relevant updates to the user devices.

11 Claims, 44 Drawing Sheets

(56) References Cited

U.S. PATENT DOCUMENTS

| | | |
|---|---|---|
| 2003/0105650 A1 | 6/2003 | Lombardo et al. |
| 2004/0210458 A1 | 10/2004 | Evans et al. |
| 2005/0015279 A1 | 1/2005 | Rucker |
| 2005/0215867 A1* | 9/2005 | Grigsby .............. G06F 19/3481 600/300 |
| 2006/0241977 A1 | 10/2006 | Fitzgerald et al. |
| 2006/0293916 A1 | 12/2006 | Somberg |
| 2007/0122783 A1 | 5/2007 | Habashi |
| 2007/0162310 A1* | 7/2007 | Schmidt ................ G06F 19/325 705/3 |
| 2007/0168225 A1 | 7/2007 | Haider et al. |
| 2008/0097965 A1 | 4/2008 | Alsafadi |
| 2008/0103814 A1 | 5/2008 | Fabius et al. |
| 2008/0103828 A1 | 5/2008 | Squilla et al. |
| 2008/0243542 A1 | 10/2008 | Hammond et al. |
| 2008/0312959 A1 | 12/2008 | Rose et al. |
| 2009/0132580 A1 | 5/2009 | James et al. |
| 2009/0276246 A1* | 11/2009 | Haskell ................ G06Q 10/06 705/3 |
| 2010/0198614 A1 | 8/2010 | Chopra et al. |
| 2010/0223071 A1 | 9/2010 | Kland et al. |
| 2010/0274579 A1* | 10/2010 | Marten ................ G06F 19/325 705/2 |
| 2011/0071851 A1* | 3/2011 | Alden .................... G06Q 10/06 705/3 |
| 2011/0161107 A1* | 6/2011 | Goldberg ............ G06F 19/3418 705/3 |
| 2011/0166882 A1 | 7/2011 | Ragazzi |
| 2011/0246220 A1* | 10/2011 | Albert .................... G06Q 50/22 705/2 |
| 2011/0301982 A1 | 12/2011 | Green, Jr. et al. |
| 2012/0059669 A1 | 3/2012 | Whittenburg et al. |
| 2012/0065987 A1* | 3/2012 | Farooq .................. G06F 19/328 705/2 |
| 2012/0078662 A1 | 3/2012 | Olivarez |
| 2012/0232930 A1 | 9/2012 | Schmidt et al. |
| 2012/0239418 A1* | 9/2012 | Flowers ................ G06Q 50/22 705/2 |
| 2012/0278095 A1 | 11/2012 | Homchowdhury et al. |
| 2013/0238348 A1* | 9/2013 | Kim .................... G06F 19/3418 705/2 |
| 2014/0257838 A1 | 9/2014 | Karra et al. |
| 2014/0330581 A1 | 11/2014 | Billings et al. |

FOREIGN PATENT DOCUMENTS

| | | | |
|---|---|---|---|
| EP | 1788502 A1 | 5/2007 | |
| EP | 1358745 B1 | 12/2008 | |
| EP | 1331874 B1 | 8/2009 | |
| JP | 2003256570 A | 9/2003 | |
| JP | 2012053632 A | 3/2012 | |
| KR | 20120082041 A | 7/2012 | |
| WO | WO-2006116529 A2 * | 11/2006 | ............ G06Q 10/06 |
| WO | WO-2008030249 A1 | 3/2008 | |
| WO | WO-2014178908 A1 | 11/2014 | |

OTHER PUBLICATIONS

International search report and written opinion dated Feb. 14, 2014 for PCT/US2013/061744.
Office action dated Feb. 8, 2016 for U.S. Appl. No. 14/025,611.
Office action dated Jul. 7, 2015 for U.S. Appl. No. 14/025,611.
Office Action dated Jul. 26, 2017 for U.S. Appl. No. 14/025,611.
Office Action dated Dec. 22, 2016 for U.S. Appl. No. 14/025,611.
U.S. Appl. No. 14/025,611 Office Action dated Feb. 7, 2018.

* cited by examiner

NETWORK SYSTEM OF INDIVIDUAL USER DEVICES TO GENERATE GROUP IMPLEMENTED TREATMENT PLAN

CROSS-REFERENCE

This application is a continuation of U.S. patent application Ser. No. 14/025,611, filed Sep. 12, 2013, which claims the benefit of Provisional Patent Application No. 61/818,310, filed May 1, 2013, which are incorporated herein by reference in their entirety and to which applications we claim priority under 35 U.S.C. § 120.

BACKGROUND OF THE INVENTION

Healthcare is becoming an ever larger sector in the national economy. The costs of healthcare are also rising, at almost an unsustainable rate. Among the contributors to rising healthcare costs is inefficient patient care management. The formation of treatment plans for patients and the management of their care is mandated by regulation to assure coordinated, efficient care. These plans are still routinely performed in archaic, inefficient, and ultimately economically costly ways. They do not meet the goal of coordinated, efficient care and are not collaborative. Therefore, new technologies for healthcare provider collaboration, the formation of treatment plans, and the management of ongoing care are greatly desired.

SUMMARY OF THE INVENTION

Systems and methods are provided for creating and implementing multi-disciplinary treatment plans. The systems and methods provided can allow healthcare and medical professionals and providers of various disciplines to collaborate and/or coordinate in forming a patient treatment plan and subsequently managing patient care in accordance with this plan.

A modular application referred to as the Multi-Disciplinary Treatment Plan (MDTP) is provided. The MDTP can address the regulatory and collaborative care requirements for clinical treatment planning of patients in team care settings; e.g., behavioral health, rehabilitation, and acute care nursing. The MDTP can assure that a patient is being treated in a holistic manner, and to assure the consistency of that treatment, while still allowing for the individualization of care. The MDTP is adapted for use in a team environment, and can give a concise overview of a patient's care problems, and how they are being addressed. The MDTP can enhance communication and collaboration by focusing all team members on the issues most important to a patient's care.

Generally, the MDTP is based on a Component framework, meaning that the application the user sees may actually be composed of functional components most suited to the user's role in the patient care. Since the MDTP is typically used in a team environment, all users typically view the same window; however, the plan is typically created by individual team members documenting their contribution to the shared plan window, while in conference with the entire team. It documents the decisions made by individuals and the team individually by the admitting physician or admitting team member, and may be updated individually. Conferencing can be in person face to face, or virtual.

An aspect of the disclosure provides a method of creating a treatment plan for a patient and a computer program product comprising a computer-readable medium having computer-executable code encoded therein adapted to execute the method. Patient information is received in a patient planning system, which may be configured to implement the computer program product. Input from a team of healthcare or medical professionals is received based on the received patient information. A treatment plan for the patient is formed based on this received input. Typically, the team of healthcare or medical professionals is comprised of healthcare or medical professionals across a plurality of disciplines. Accordingly, the treatment plan formed is a Multi-Disciplinary Treatment Plan (MDTP). Members of the team of healthcare or medical professionals may hail from a variety of healthcare or medical disciplines, including but not limited to allergy and immunology, anesthesiology, cardiology, cardiovascular surgery, clinical laboratory sciences, dermatology, dietetics, emergency medicine, endocrinology, family medicine, forensic medicine, gastroenterology, general surgery, geriatrics, gynecology, hematology, infectious disease, intensive care medicine, medical research, nephrology, neurology, neurosurgery, obstetrics and gynecology, oncology, ophthalmology, oral and maxillofacial surgery, orthopedic surgery, otorhinolaryngology or ENT, palliative care, pathology, pediatrics, pediatric surgery, physical medicine and rehabilitation or psychiatry, plastic surgery, podiatry, proctology, psychiatry, pulmonology, radiology, rheumatology, stomatology, surgical oncology, thoracic surgery, transplant surgery, urgent care medicine, urology, and vascular surgery. The composition of the team will typically depend on the type of patient and type of patient problem. Using the MDTP, the team can create and implement a holistic and collaborative treatment regimen for the patient, often needed most for longer multi-disciplinary care encounters where the outcome depends on the coordination and not on any one intervention or discipline.

The treatment plan will typically be updated in the treatment planning system as the course of therapy performed on the patient based on the treatment plan progresses. An active shared plan will often be on the chart at all times and may be updated routinely based on regulation and policy. The treatment plan may be updated based on further input from the team of healthcare or medical professionals. The treatment planning system may receive the further input after the team of healthcare or medical professionals have met and discussed the treatment plan and the progression of the course of the therapy.

Typically, input is received from the team of healthcare or medical professionals after the team has met and discussed a course of therapy appropriate for the patient. Prior to receiving such input, an initial treatment plan may have been formed in the treatment planning system based on the received patient information. The initial treatment plan may be created based on the received patient information, often by the admitting physician or nurse. Like the main treatment plan, the treatment planning system may be used to update the initial treatment plan as the course of initial therapy based on the initial treatment plan progresses. The initial treatment may continue until the main, comprehensive treatment plan is formed and implemented.

Another aspect of the disclosure provides a graphical user interface for creating a treatment plan for a patient. The graphical user interface comprises a generalized treatment planning section and a patient-specific section for displaying patient treatment information. The generalized treatment planning section may comprise a plurality of tabs. The plurality of tabs may comprise a templates tab for creating patient data entries, a previous plan tab for displaying a prior course of patient treatment, a details tab for displaying patient-specific data, and a tasks tab for adding or editing patient-specific tasks. Patient data entries can be created in the templates tab for one or more of patient problems, patient recovery statuses, patient treatment objectives, and patient interventions. The patient data entries in the templates tab can be dragged onto the patient-specific section of the graphical user interface. The previous plan tab may comprise entries for one or more of patient problems, patient recovery statuses, patient treatment objectives, and patient interventions. The entries in the previous plan tab can also be dragged onto the patient-specific section of the graphical user interface. The tasks tab may comprise entries for one or more of a patient problem description, a reassessment frequency, a patient problem type, a patient problem action task, a patient problem status, an entry for an appropriate healthcare or medical professional team member, comments, and tags. The tasks tab further comprises a signature box for verifying the entries. Once the entries are verified, the task is finalized and may be viewed and accessed from in the patient-specific section of the graphical user interface.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 27:
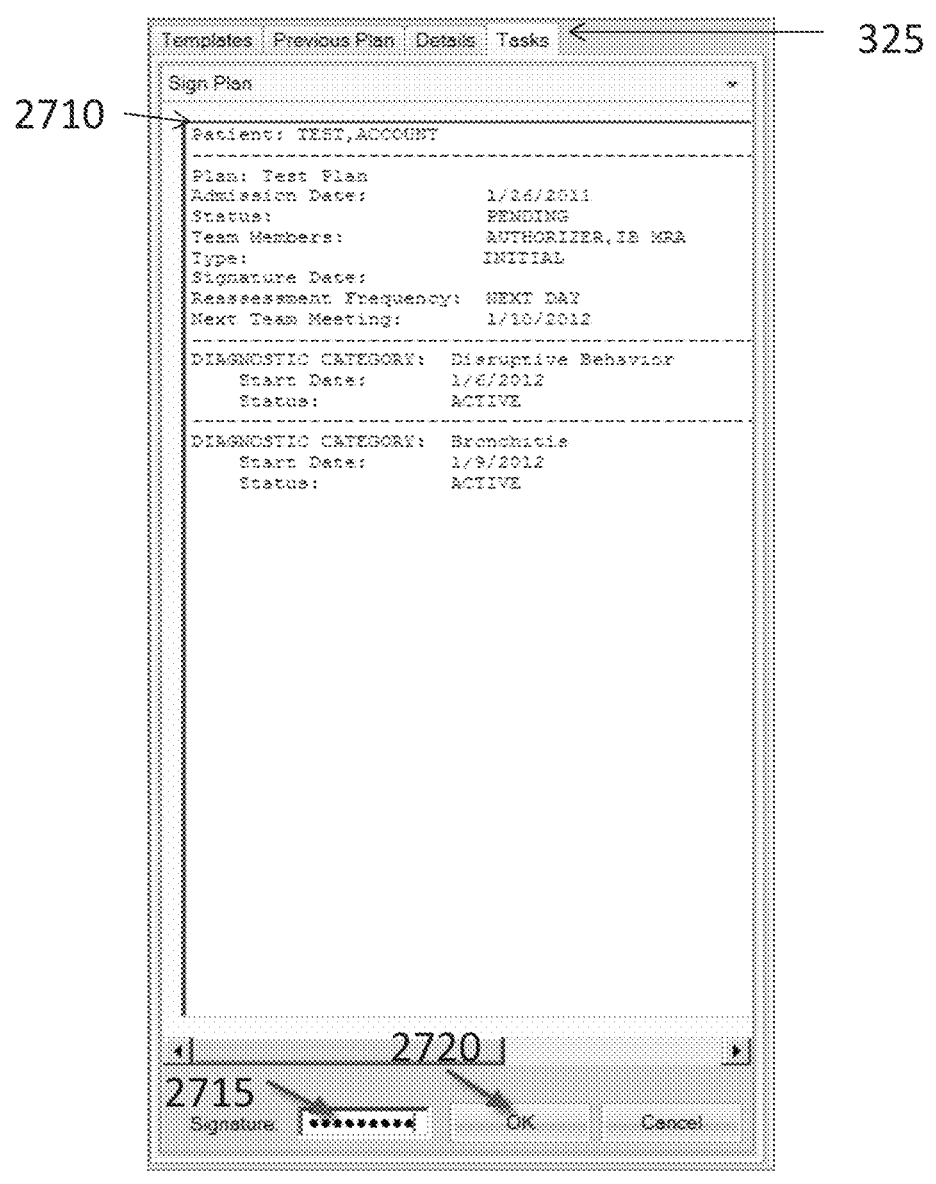

FIGS. 26 and 27 show screenshots of different portion of the MDTP application of FIG. 2 being used to sign a treatment plan;

FIGS. 31 to 49 shows screenshots of the MDTP application of FIG. 2 in use to create and implement a treatment plan according to an embodiment of the disclosure.

DETAILED DESCRIPTION OF THE INVENTION

Figure 1:
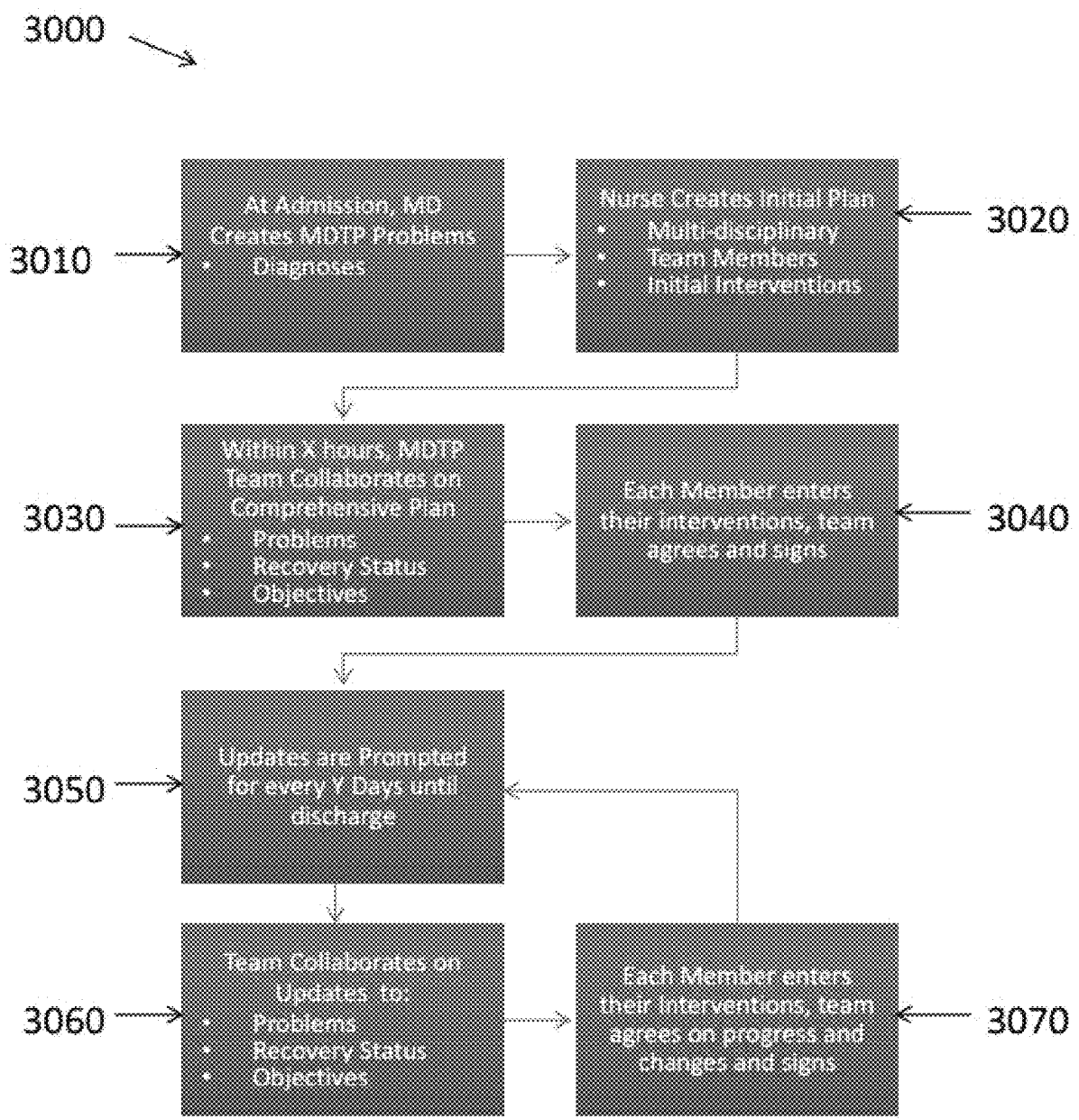
FIG. 1 shows a flowchart of a workflow process of generating, implementing, and updating a multi-disciplinary treatment plan (MDTP) according to an embodiment of the disclosure.

The disclosure provides systems and methods for creating and using multi-disciplinary treatment plans. Various aspects of the invention described herein may be applied to any of the particular applications set forth below or for any other types of user interfaces and displays, or patient care planning and management applications. The systems and methods disclosed herein may be applied in a standalone manner, or as part of an integrated software package, such as a healthcare or patient data management package or application. It shall be understood that different aspect of the disclosure can be appreciated individually, collectively, or in combination with each other.

Video displays described herein may include devices upon which information may be displayed in a manner perceptible to a user, such as, for example, a computer monitor, cathode ray tube, liquid crystal display, light emitting diode display, touchpad or touch-screen display, and/or other means known in the art for emitting a visually perceptible output. Video displays may be electronically connected to a client computer according to hardware and software known in the art. A team can view the shared plan on a monitor while each working on their portion on their computers to collaborate in conference.

In one implementation, a display page may include a computer file residing in memory which may be transmitted from a server over a network to a client computer, which can store it in memory. A client computer may receive non-transitory computer readable media, which may contain instructions, logic, data, or code that may be stored in persistent or temporary memory of the client computer, or may somehow affect or initiate action by a client computer. Similarly, one or more servers may communicate with one or more client computers across a network, and may transmit computer files residing in memory. The network, for example, can include the Internet or any network for connecting one or more clients to one or more servers.

Any discussion of a client computer may also apply to any type of networked device, including but not limited to a personal computer, server computer, or laptop computer; personal digital assistants (PDAs) such as a Palm-based device or Windows CE device; phones such as cellular phones or location-aware portable phones (such as GPS); a roaming device, such as a network-connected roaming device; a wireless device such as a wireless email device or other device capable of communicating wireless with a computer network; or any other type of network device that may communicate over a network and handle electronic transactions. Any discussion of any device mentioned may also apply to other devices.

At a client computer, the display page may be interpreted by software residing on a memory of the client computer, causing the computer file to be displayed on a video display in a manner perceivable by a user. The display pages described herein may be created using a software language known in the art such as, for example, the hypertext mark up language ("HTML"), the dynamic hypertext mark up language ("DHTML"), the extensible hypertext mark up language ("XHTML"), the extensible mark up language ("XML"), or another software language that may be used to create a computer file displayable on a video display in a manner perceivable by a user. Any computer readable media with logic, code, data, instructions, may be used to implement any software or steps or methodology. Where a network comprises the Internet, a display page may comprise a webpage of a type known in the art.

A display page according to the invention may include embedded functions comprising software programs stored on a memory, such as, for example, VBScript routines, JScript routines, JavaScript routines, Java applets, ActiveX components, ASP.NET, AJAX, Flash applets, Silverlight applets, or AIR routines.

A display page may comprise well known features of graphical user interface technology, such as, for example, frames, windows, tabs, scroll bars, buttons, icons, menus, fields, and hyperlinks, and well known features such as a "point and click" interface. Pointing to and clicking on a graphical user interface button, icon, menu option, or hyperlink also is known as "selecting" the button, icon, option, or hyperlink. Additionally, a "point and gesture" interface may be utilized, such as a hand-gesture driven interface. Furthermore, a touch-screen interface may be utilized, where touching a visual object may constitute selecting the object. Any other interface for interacting with a graphical user interface may be utilized. A display page according to the invention also may incorporate multimedia features.

Any of the client or server devices described may have tangible computer readable media with logic, code, or instructions for performing any actions described herein or running any algorithm. The devices with such computer readable media may be specially programmed to perform the actions dictated by the computer readable media.

1. Introduction

Figure 30:
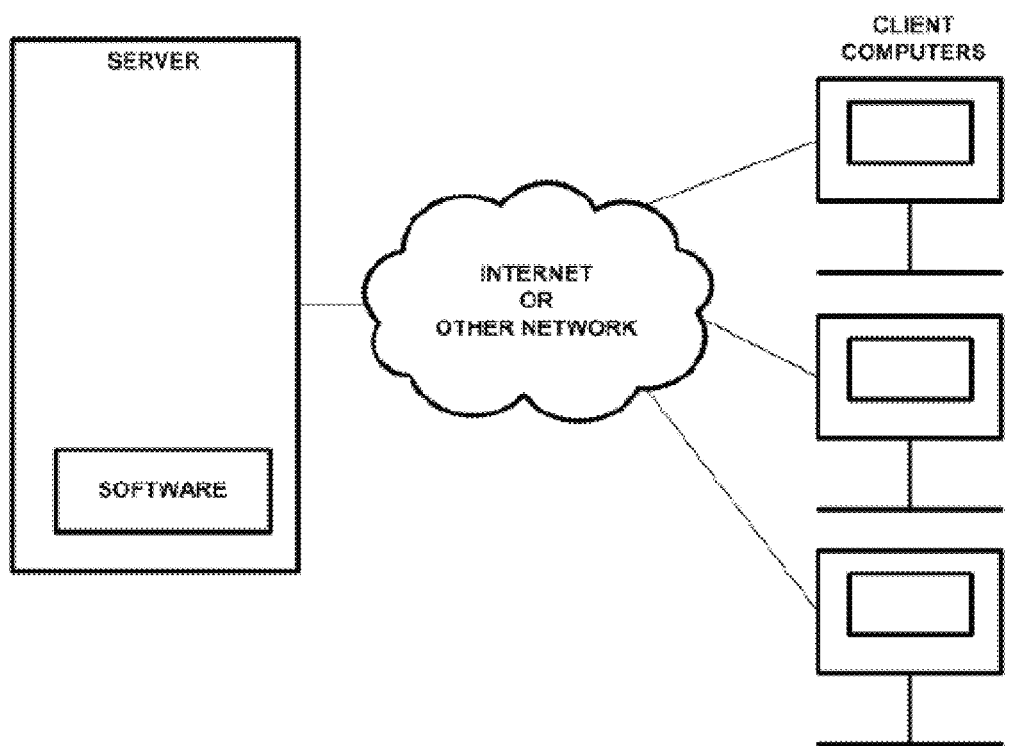
FIG. 30 shows a server communicating with a plurality of client computers over a network to generate, implement, and update the MDTP.

A modular application referred to as the Multi-Disciplinary Treatment Plan (MDTP) is provided. A user interface of the MDTP provided in accordance with the invention herein may be displayed across a network such as the Internet or an intranet, for example, a hospital intranet. For example, as shown in FIG. 30, an implementation may include a client computer comprising a video display with at least one display page comprising MDTP data.

Figure 2:
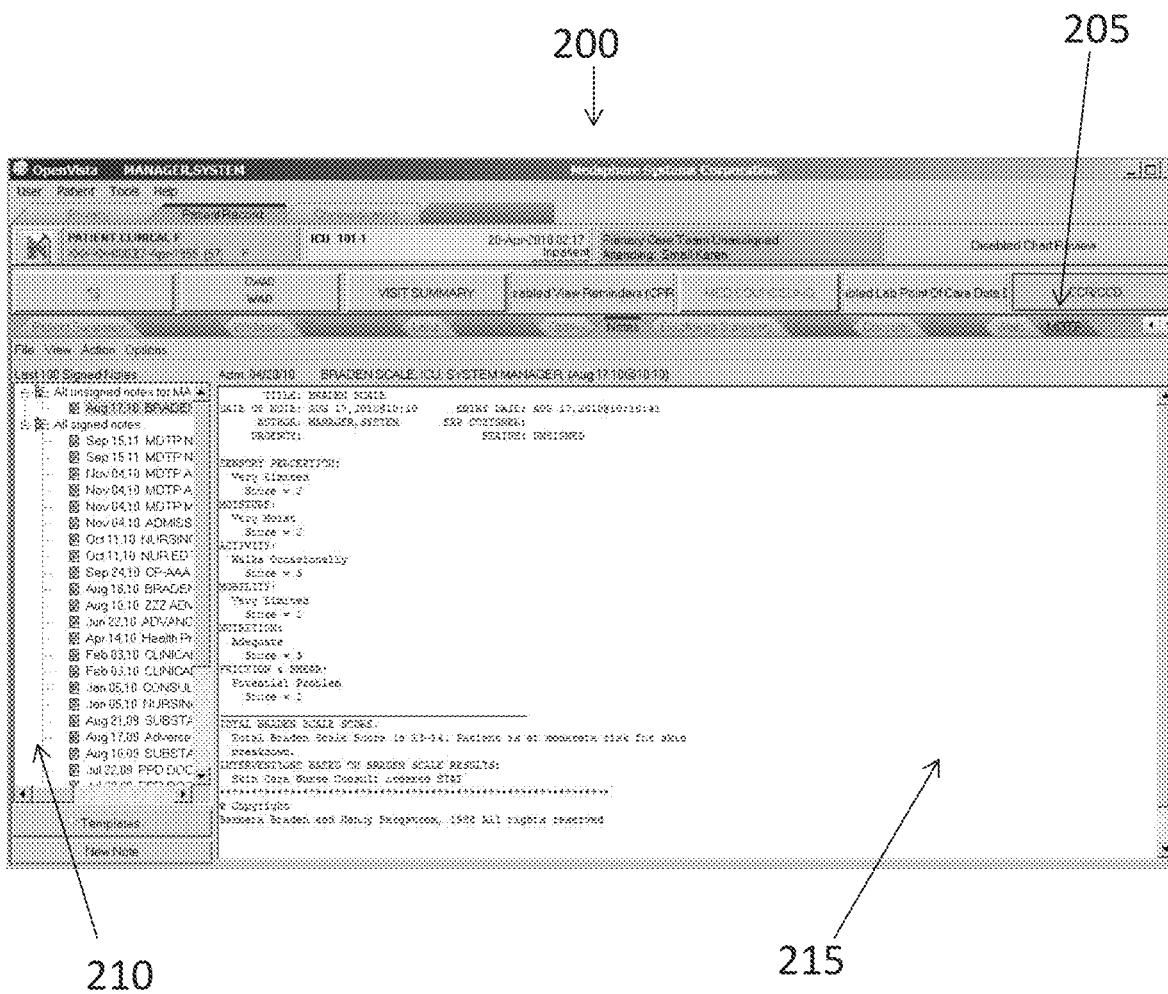
FIG. 2 shows a screenshot of the main system window to generate, implement, and update a MDTP, according to an embodiment of the disclosure.

MDTP Windows:

The MDTP is typically used in team environment. All users typically view the same window, for example, the main system window 200 as shown in FIG. 2. To access the MDTP, a user can click the MDTP tab 205 in the main system window 200.

Figure 3:
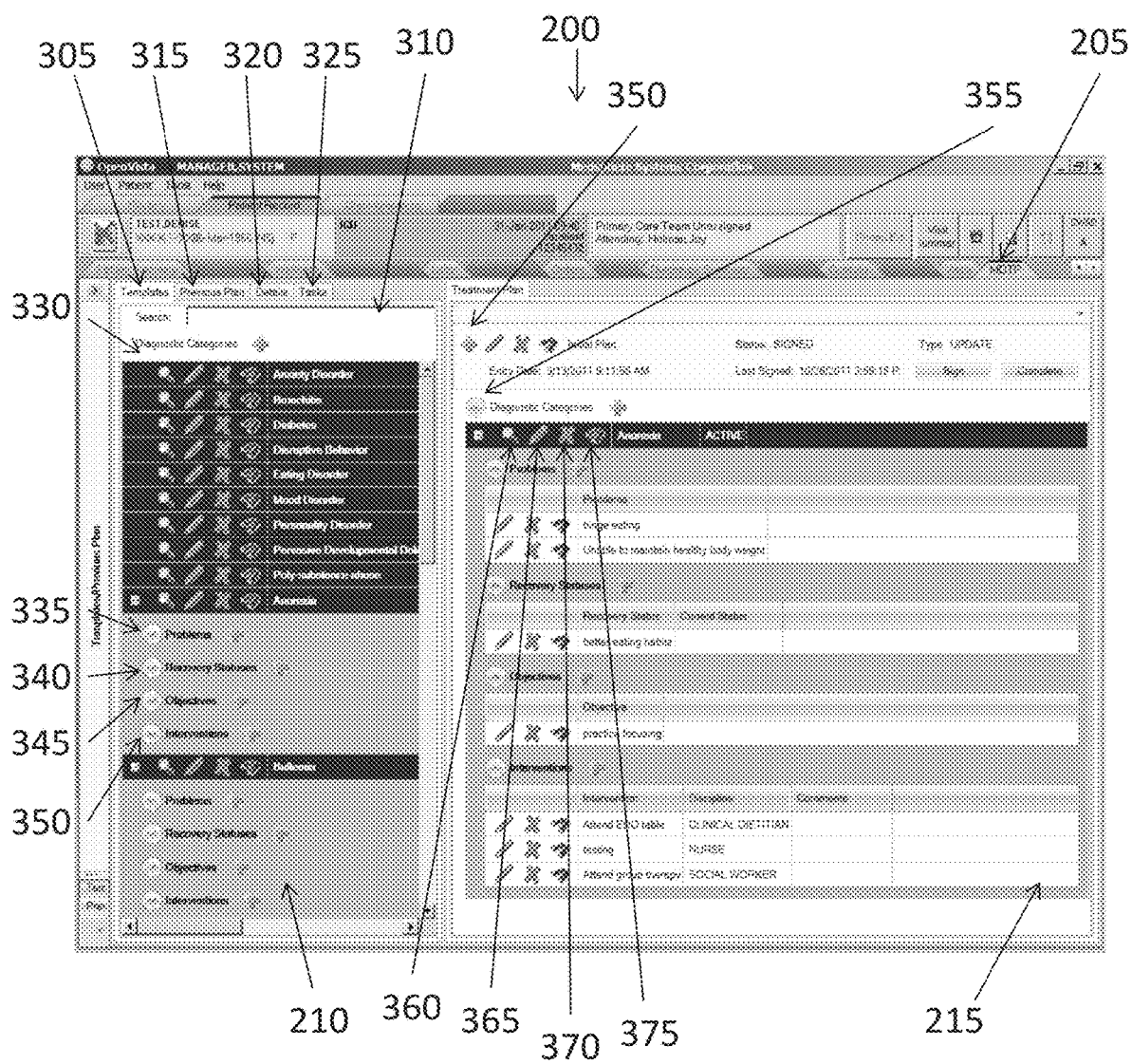
FIG. 3 shows a screenshot of a selected MDTP tab in the main system window of FIG. 2.

MDTP Tab:

As shown in FIGS. 2 and 3, the MDTP tab 205 is generally divided into two panes: a plan options pane or left pane 210 and a patient-specific treatment plan or right pane 215. Referring to FIG. 3, the MDTP tab 205 usually displays the following sub-tabs: a templates tab 305, a search field 310, a previous plan tab 315, a details tab 320, and a tasks tab 325.

Templates: The templates tab 305 can comprise a number of menu items including diagnostic categories 330, problems 335, recovery statuses 340, objectives 345, and interventions 350 that will typically have been pre-defined by each institution, e.g., an individual hospital for which the MDTP is customized for. They will usually be the most commonly-used items, and are intended to provide a quick and easy way to select items, as well as provide consistency through throughout each organization. In many embodiments, only the MDTP ADMIN key may add, modify, or delete template entries.

Search: Although all items are typically listed on the templates tab 305, you can filter items by typing one or more terms (separated by commas), such as "Anxiety," that may be associated with the item in the search field 310 on the templates tab 305, and then by pressing Enter.

Tags: If tags were added to the Tags field when an item was created, the user can then type the first few letters (or the entire word) of some keywords associated with the item, and after pressing Enter, the appropriate item shows at the top of the diagnostic categories list 330.

Previous Plan: If a patient has a multi-disciplinary treatment plan from a previous encounter, it can display on the previous plan sub-tab 315 for a time period set by the relevant institution. Items from the previous plan may be selected and included (pulled) into the current plan, if relevant. For example, if a patent's last plan was for an acute admission, and a new plan is now being created in a lower-acuity care site after transfer, older diagnostic categories 330 can be easily pulled into the new plan and completely different objectives 345 and interventions 350 may be defined.

Details: Clicking a patient-specific item in the treatment plan of the right panel or pane 215 (for example, a specific intervention), can display the details in the details tab 320 on the left panel or pane 210 as view-only. This display can enable multiple team members to view the same item at the same time.

Tasks: When a patient-specific item in the treatment plan of the right panel or pane 215 (for example, a specific intervention) is added or edited, it can appear on the tasks sub-tab 325. This can indicate that it is actively being worked on, and no other user may access the item for editing, although it may be viewed. During this time, task information viewed by another user can be the information displayed before starting to edit the item. In many embodiments, when the user edits any item, the user must click either OK or Cancel before another item in the task pane can be accessed.

Icons: The user can click one of a number of applicable icons to perform various tasks in the treatment plan. The user can click the new diagnostic category icon 350 to create a new diagnostic category or a new item within a diagnostic category and then completing the task tab 325. The user can click the diagnostic categories expansion icon 355 to expand the diagnostic category and show problems, recovery statuses, objectives, and interventions. The user can click the filter icon 360 to filter items in the templates tab 305 to only those associated with the diagnostic category selected. The filter icon 360 can also be used to expand the diagnostic categories 330 menu in the templates tab 305 to show the associated problems 335, recovery statuses 340, objectives 345, and interventions 350. The user can click the edit icon 365 to make edits. An edit template pane may then open in the tasks tab 325. The user can then edit or add information in the fields as needed and then click OK. The user can click the delete icon 370 to delete a treatment plan, diagnostic category, or any item with a diagnostic category upon a refresh of the data. The user can click the details tab icon 375 to open the details tab 320.

II. Patients

Entering Patient Information: Patient information can be entered into the system using the main system window 100 when a patient is admitted to a hospital. Once the patient information is recorded, the admitting physician can begin the process of creating an initial Treatment Plan. The admitting nurse can then review the Treatment Plan created by the admitting physician and update the plan items necessary to care for the patient until the full multi-disciplinary team meets. The first time the Multi-Disciplinary Treatment Team meets to discuss a specific patient, they can complete the Treatment Plan. Thereafter, the Team can meets on a regular basis and updates the Treatment Plan.

III. Treatment Plans

Treatment Plan Overview: Initial Treatment Plans may be created by the admitting physician, or a team member. A Treatment Plan may comprise one or more Diagnostic Categories. Each Diagnostic Category can have one or multiple Problems, Recovery Statuses, Objectives, and Interventions. Plans can easily be created or edited by: pulling items such as Problems, Recovery Statuses, Objectives, and Interventions from site-defined templates; pulling items from the patient's previous Plan; or, creating new Diagnostic Category items. The admitting physician or admitting team member will typically be responsible for entering the Diagnostic Categories and associated Problems. Problems entered into MDTP and associated with each diagnosis should be the most salient syndromal features for the patient at this point in their illness. This grouping of problems can equate to a Symptom Complex, or those clinical entities that tend to move together, are treated together, and are currently manifesting in this particular patient.

Figure 4:
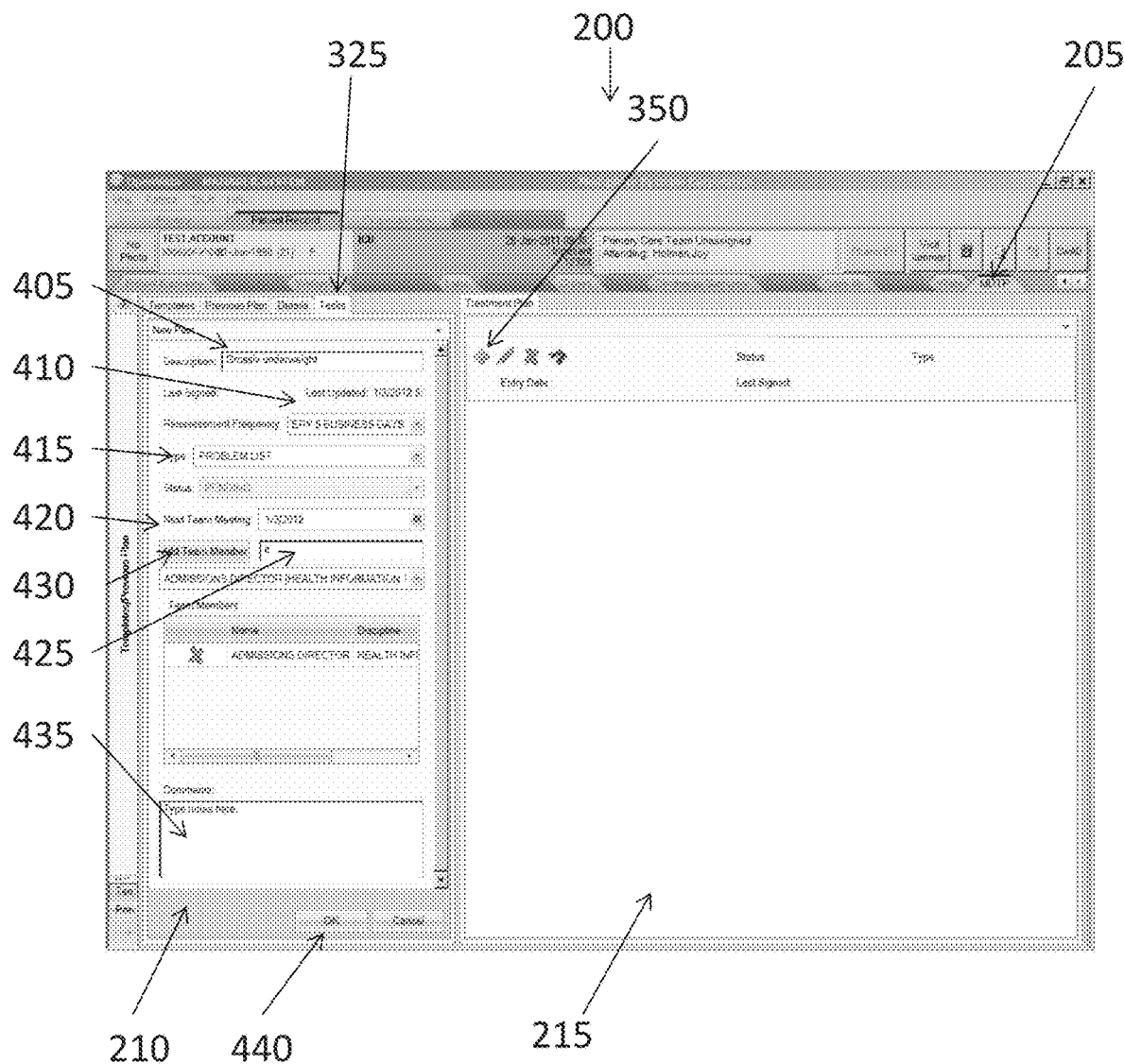
FIG. 4 shows a screenshot of the MDTP application of FIG. 2 being used to create a new treatment plan.

Creating a Treatment Plan (Admitting Physician): Referring to FIG. 4, a treatment plan can be created with the steps discussed as follows. One, the MDTP tab 205 can be clicked in the main system window 200. Two, the new diagnostic category icon 250 in the upper-left corner of the treatment plan information pane 215 can be clicked; and, a new plan may then open in the tasks tab 325 on the left pane 210. Three, in the description field 405, the admitting physician can create a new treatment plan by typing the name of the plan according to a site-defined naming convention and then clicking the OK button 440 at the bottom of the task tab 325 to accept all defaults. If needed, the admitting physician may modify or add any information by following further steps.

The reassessment frequency drop-down menu 410 can be used to select the applicable frequency from the drop-down list. Next day will typically be the default setting.

The type drop-down menu 415 can be used to select the applicable type from the drop-down menu. Problem List will typically be the default setting.

In the next team meeting drop-down entry 420, a date can be entered or the calendar icon can be clicked to select a date.

In the open field 425 next to the Add Team Member button 430, the user can begin to type the first few letters of the team member the user wants to add and then click the button 430. The user can also click the down-arrow in the field below the Add Team Member button 430 and select from a list. The entered team member's name can then be added to the Team Members section. This can also create a notification for the team member for the next team meeting.

In the comments box 435, a user can type a note, if applicable.

By clicking the OK button 440 at the bottom of the tasks tab or pane 325, a new plan can be created for the patient and may appear in the treatment plan pane 215 on the right of the main system window 200.

Figure 5:
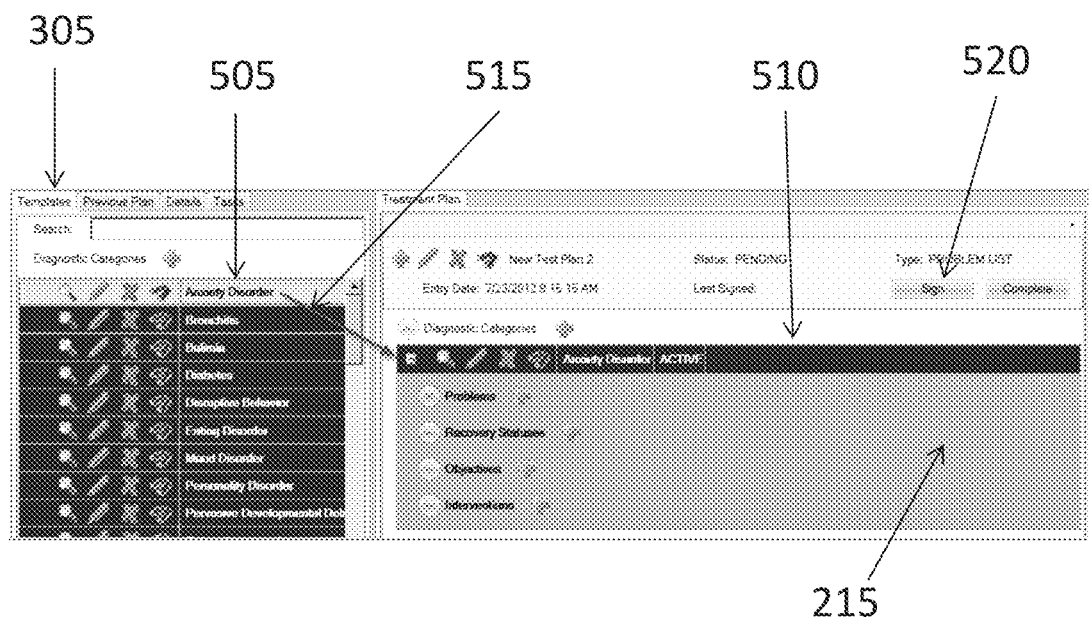
FIG. 5 shows a screenshot of a portion of the MDTP application of FIG. 2 being used to add a diagnostic category to the new treatment plan.
Figure 6:
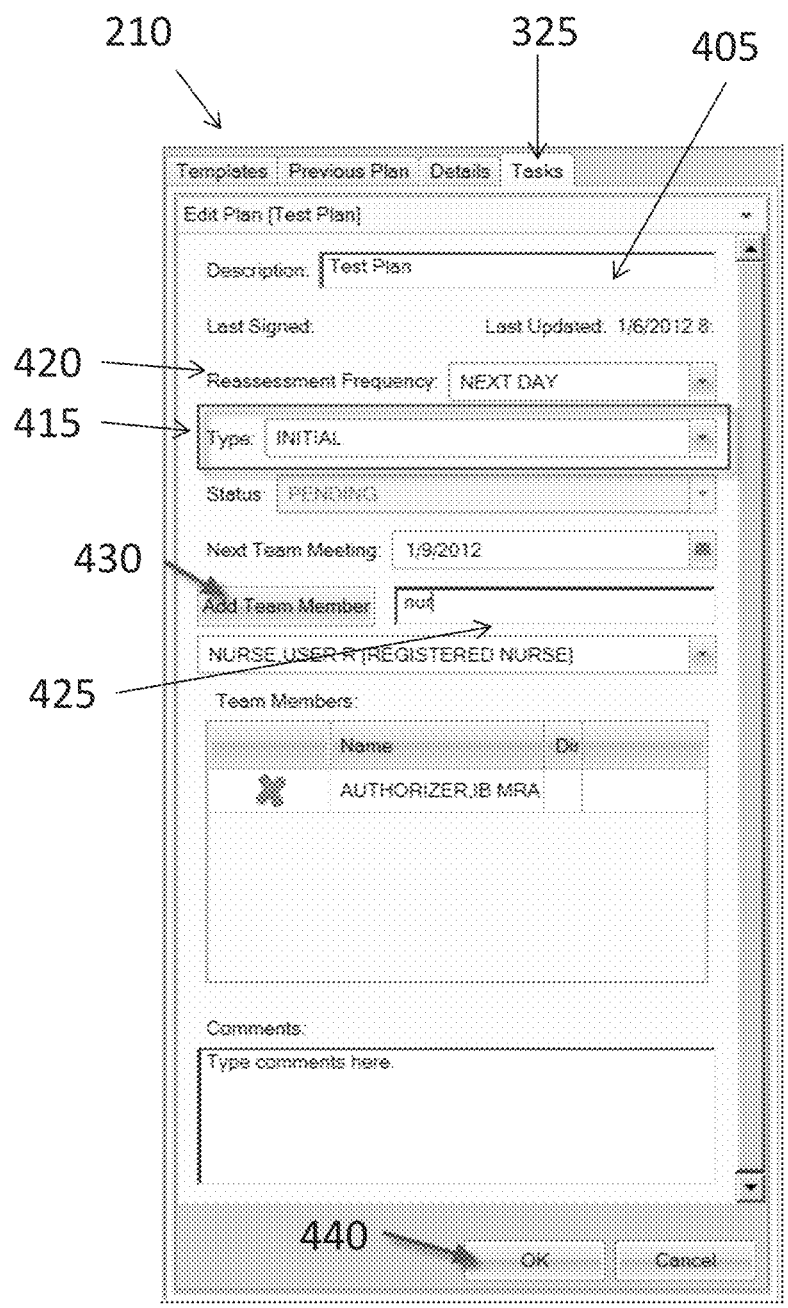
FIG. 6 shows a screenshot of a portion of the MDTP application of FIG. 2 being used to edit the treatment plan.

Referring now to FIG. 5, from the templates tab 305, the user can click to select a Diagnostic Category 505 for the patient. In many embodiments, the Ctrl key can be held down while clicking to select multiple Diagnostic Categories 505. The user can then drag the selected Diagnostic Category 505, for example, Anxiety Disorder, and drop in into the blue section 510 on the treatment plan pane 215. This is shown by arrow 515 in FIG. 5. The plan can then be signed by the user by clicking the sign button 520.

IV. Adding Treatment Plan Information (Admitting Nurse)

Within the given timeframe from admittance, the admitting nurse can then review the Treatment Plan created by the admitting physician and then updates the plan items necessary to care for the patient until the full multi-disciplinary team meets. In many embodiments, the admitting nurse may not necessarily be part of the MDTP Team but may generally be the nurse who is on duty at the time the patient is admitted. Once the Plan is created, the admitting nurse can sets the next meeting date, and assigns a team member or members to treat the patient and adds any additional Diagnostic Categories 505.

From the Treatment Plan tab 215 on the right side of the screen, the user can click the edit icon 365. The Tasks tab 325 can then open on the left side 210 of the screen. In many embodiments, if needed, the admitting nurse may modify or add any information by following the following steps. In the Type drop-down menu 415, the user can select the applicable type. Initial is the default. When Initial is selected, the Reassessment Frequency updates to Next Day, and the Next Team Meeting date updates to the next day's date. In many embodiments, once the Initial plan is signed, the system automatically may update the Type to Comprehensive.

In the open field 425 next to the Add Team Member button 430, the user can begin to type the first few letters of the team member the user wants to add, and then click the Add Team Member button 430. Then, the user can click the OK button 440 at the bottom of the tasks tab 210. In many embodiments, when editing any item, the user must either click OK or Cancel before another item in the Tasks tab 210 can be accessed. This saves (or cancels) the information entered. Otherwise, a warning message appears, indicating there are active tasks. After updating the Treatment Plan, the user can sign it, which creates a Note in the main system.

V. Completing the Plan (Multi-Disciplinary Team)

Initial Team Meeting—Comprehensive MDTP Development

The first time the Multi-Disciplinary Treatment Team meets to discuss a specific patient, they can complete the Treatment Plan to include all Problems, Recovery Statuses, Objectives, and Interventions for all Diagnostic Categories. First, from the Templates tab 305, one or more users can select any additional Problems 335, Recovery Statuses 340, Objectives 345, and Interventions 350 that apply for this patient and drag and drop it to the Diagnostic Categories section in the Treatment Plan tab 115. In many embodiments, multiple items may be selected by holding down the Ctrl key and clicking the desired items individually. In many embodiments, if an item is not available in the site-defined Diagnostic Categories selections, it may be created. However, created items may not become a Template item and may not be used or selected again for a different patient. To filter the List of Items on the Template tab 305, the user can click the filter icon 360 next to the relevant Diagnostic Category, and/or type one or more terms (separated by commas) that may be associated with the item (such as, Anxiety) in the Search field, and then press Enter. If the user needs to edit the Diagnostic Categories items created from the template, the user can edit the Diagnostic Categories as described below. Second, the user can complete the Diagnostic Categories items, as needed, following the steps below.

Figure 7:
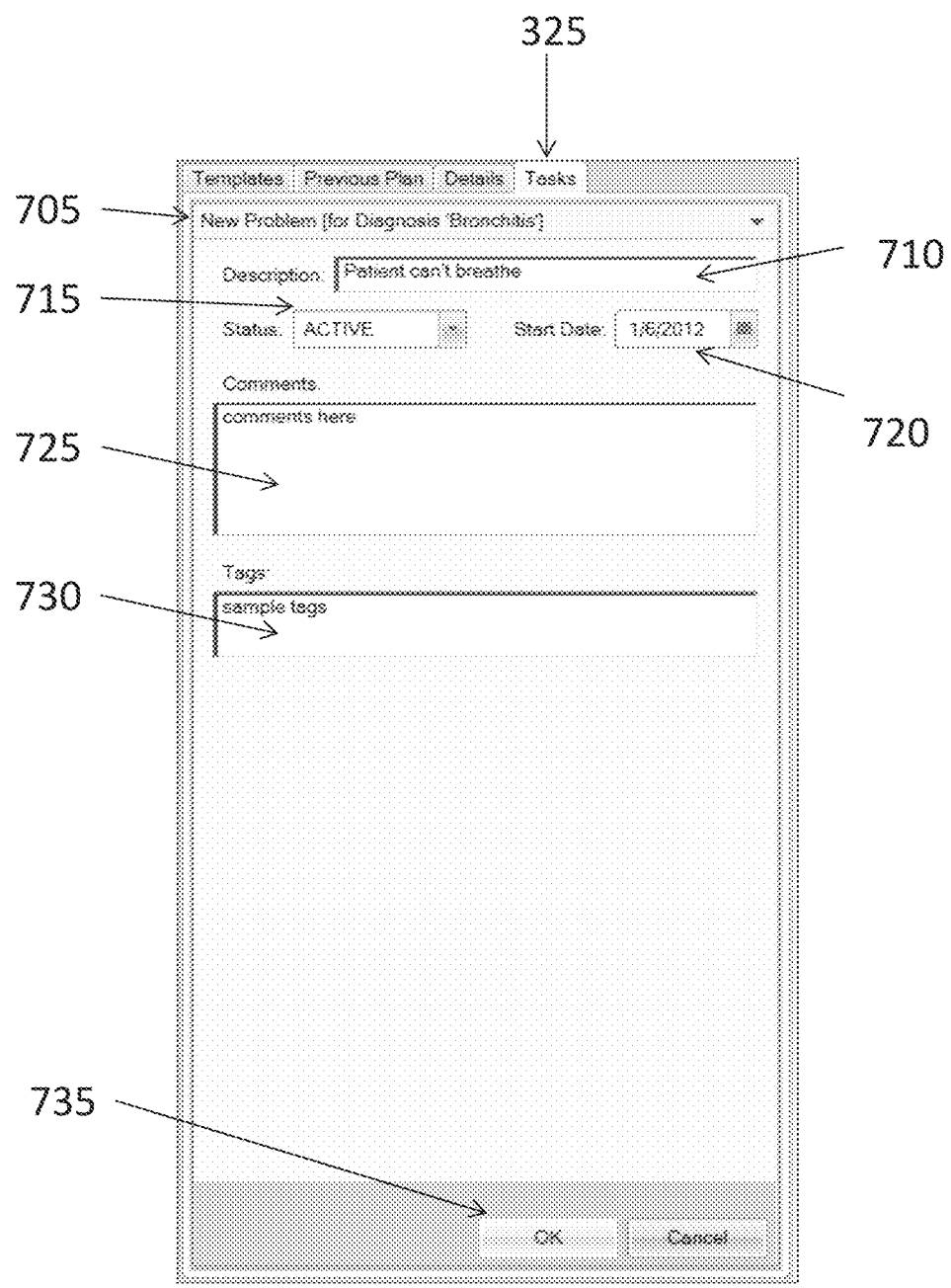
FIGS. 7 and 8 show screenshots of different portions of the MDTP application of FIG. 2 being used to add problem tasks information.
Figure 8:
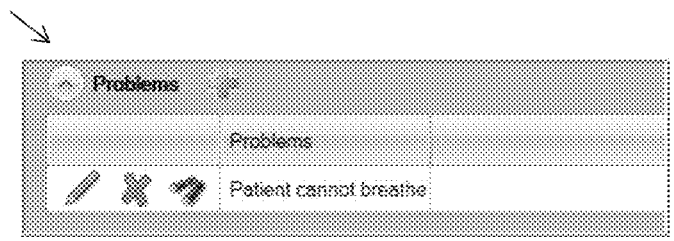

Problems: Referring now to FIG. 7, after adding a Problem to the Treatment Plan tab 215, the New Problem pane 705 will open in the tasks tab 325. In the description box 710, the user can type a description of the problem. In the status pull-down menu 715, one of the following can be selected: Active, Inactive, or Resolved. The calendar icon can be clicked in the Start Date section 720 to select a date. In the comments box 725, a note can be typed as needed. In the tags box 730, any tags can be added as needed. The OK button 735 can then be clicked to update the Problem in the Treatment Plan tab 215 as shown by the relevant portion 215a of the Treatment Plan tab 215 in FIG. 8.

Figure 9:
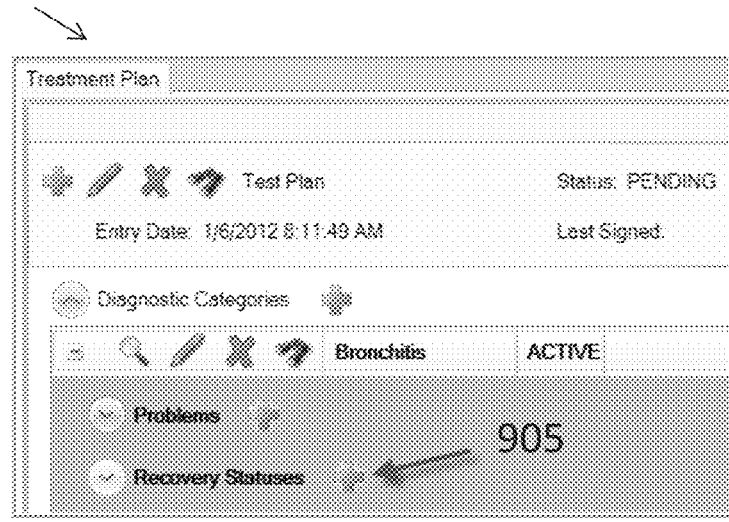
FIGS. 9, 10, and 11 show screenshots of different portions of the MDTP application of FIG. 2 being used to update recover status information.
Figure 10:
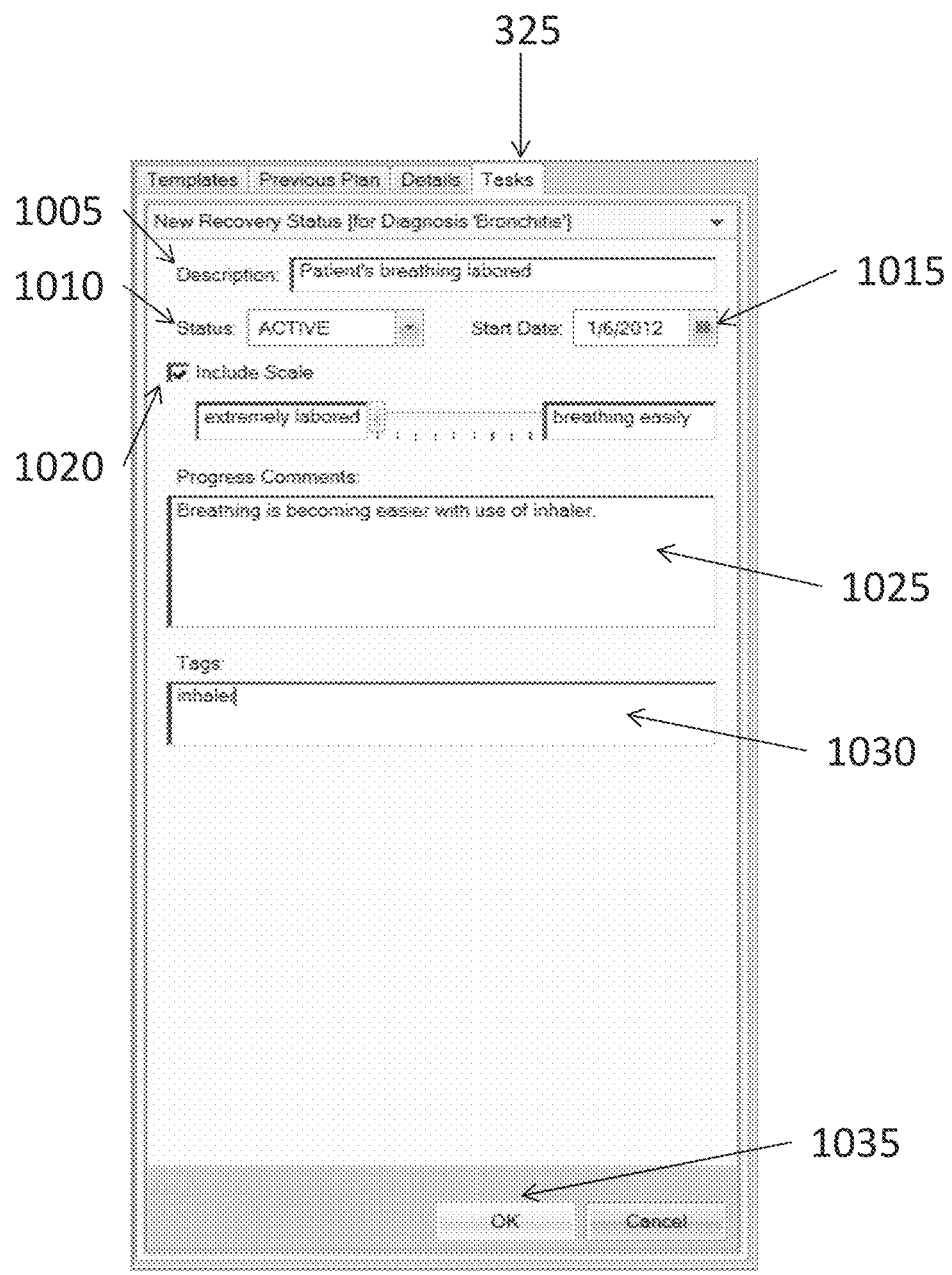
Figure 11:
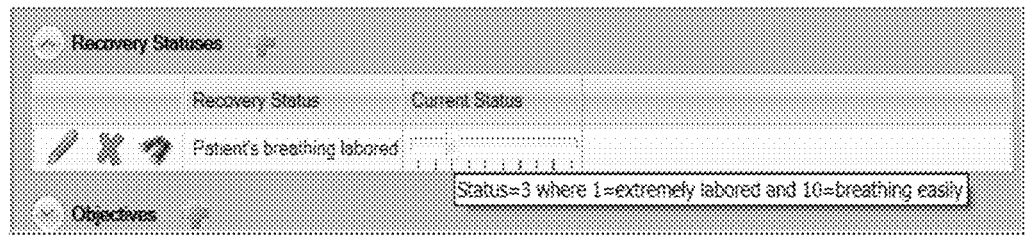

Recovery Statuses: Referring to FIG. 9, after adding a Recovery Status to the Treatment Plan tab 215, the Add Recovery Status icon 905 next to the Recovery Statuses text can be clicked. This will open the tasks tab 325 with a New Recovery Status, for example, for Diagnosis "Bronchitis" as shown in FIG. 10. In the description box 1005, the user can type a description for the recovery status. In the status pull-down menu 1010, the user can select Active or Inactive, as applicable. The calendar icon 1015 can be clicked to select a date. If applicable, the user can click the checkbox 1020 to include a scale. In the fields before and after the scale, the user can type a description of the item being measured, and then use the sliding scale to indicate the level. In the example shown by FIG. 10, the patient's ease of breath is used, and is tracked from extremely labored to breathing easily. In the Progress Comments box 1025, a note about the patient's progress can be entered. If applicable, any tags the user may want to associate with the present template can be entered in the tabs box 1030. Finally, the OK button 1035 can be clicked to update the Recovery Status in the Treatment Plan tab 215 as shown by the relevant portion 215b of the Treatment Plan tab 215 in FIG. 11.

Figure 12:
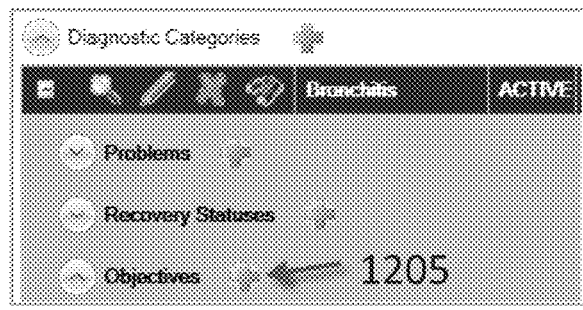
FIGS. 12, 13, and 14 show screenshots of different portions of the MDTP application of FIG. 2 being used to update information concerning patient care objectives.
Figure 13:
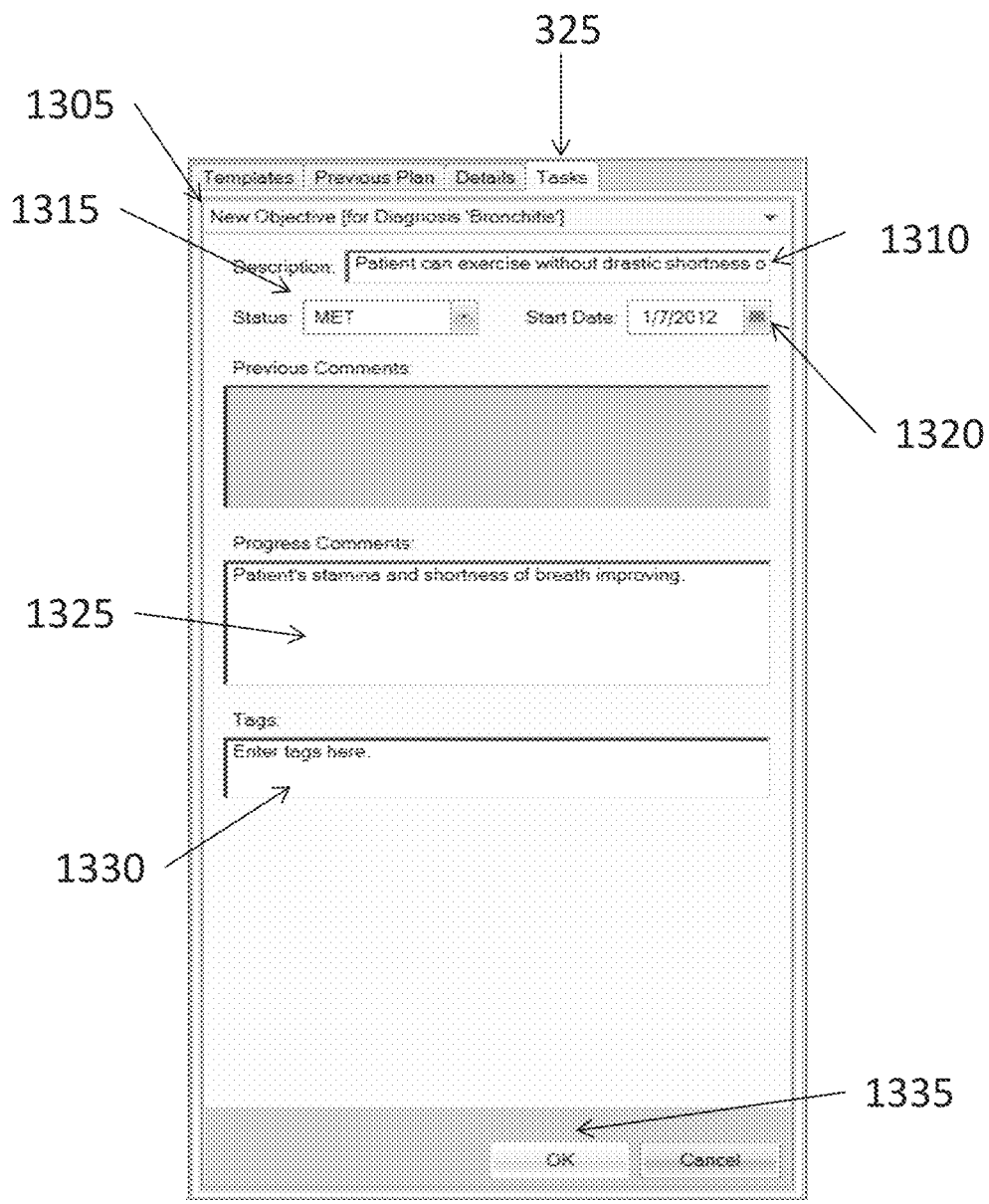
Figure 14:

Objectives: Referring to FIG. 12, after adding an Objective to the Treatment Plan tab 215, the user can click the add new objective icon 1105 next to the Objectives text. This will open the Tasks tab 325 with a New Objective tab 1305, for example, for Diagnosis "Bronchitis" as shown in FIG. 13. In the Description box 1310, the user can type a description for the objective. In the Status pull-down menu 1315, the user can select one of Met, Not Met, or Other as applicable. The calendar icon 1320 next to the Start Date section can be clicked to select a date. In the Progress Comments box 1325, the user can type any notes about the patient's progress. In the Tags box 1330, any tags, as applicable, may be entered. The OK button 1335 can then be clicked to update the Objective in the Treatment Plan tab 215 as shown by the relevant portion 215c of the Treatment Plan tab 21c in FIG. 14.

Figure 15:
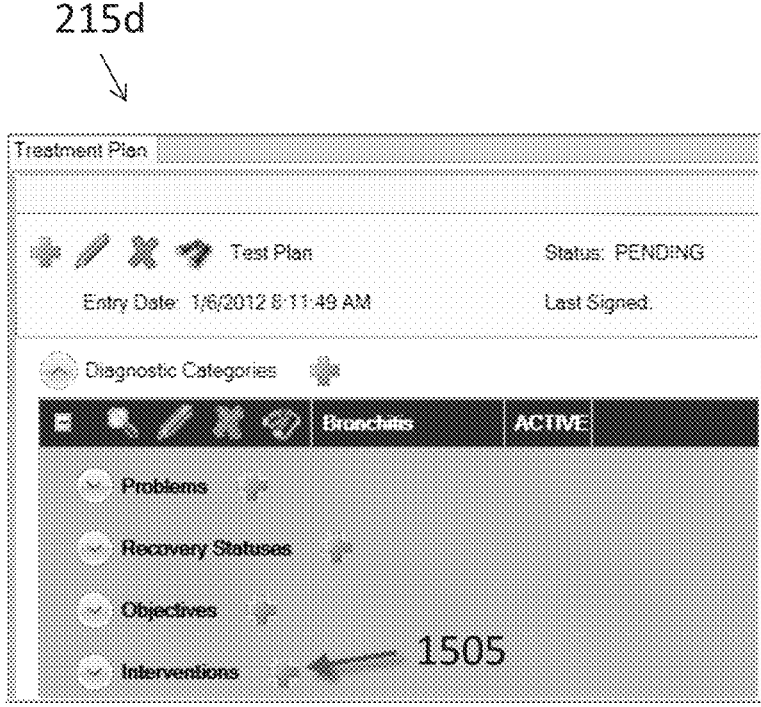
FIGS. 15, 16, and 17 show screenshots of different portions of the MDTP application of FIG. 2 being used to update interventions information.
Figure 16:
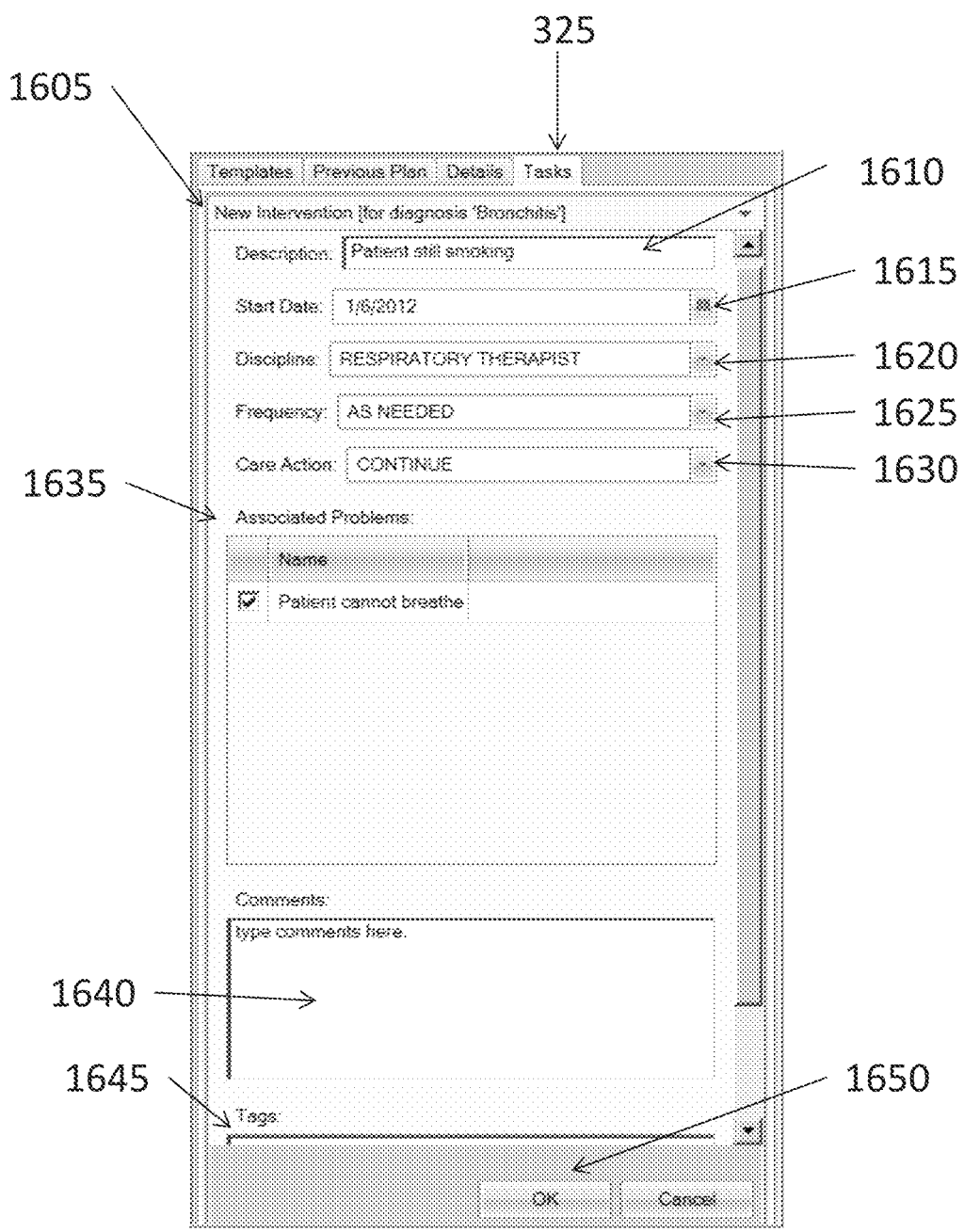
Figure 17:

Interventions: After adding an Intervention to the Treatment Plan tab 215, the user can click the Add Intervention icon 1505 next to the Interventions text in the relevant part 215d of the Treatment Plan tab 215 shown in FIG. 15. As shown in FIG. 16, the Tasks tab 325 can then open with a New Intervention 1605, for example, for Diagnosis "Bronchitis". In the Description box, the user can type a description for the intervention. In the Start Date section, the user can click the calendar icon 1615 to select a date. In the Discipline section, the user can use the drop-down menu 1620 to select the applicable specialist, for example, Clinical Dietitian. In the Care Action section, the user can use the drop-down menu 1630 to select one of the following: Continue, Discontinue, Completed, or Add. In the Associated Problems section 1635, the user can click to select any problems associated with the intervention. In many embodiments, any Problems previously entered for this Diagnostic Category will appear in the Associated Problems section 1635. This matrixing can eliminate the redundancy often found in traditional treatment plans based on a tree structure in which interventions can become redundant, making documentation of progress burdensome or incomplete. In the Comments box 1640, the user can type any applicable notes. In the Tags box 1645, the user can type any applicable tags. Finally, the user can click the OK button 1650 to update the Intervention in the Treatment Plan tab 215 as shown with the relevant part 215e of the Treatment Plan tab 215 shown in FIG. 17.

The Treatment Plan can then be completed by clicking the edit icon 365 in the Treatment Plan tab 215. This will open the Task tab 325 on the left side of the screen, for example, as shown in FIG. 4. If needed, in the Reassessment Frequency drop-down menu 410 can be used to select the applicable frequency which may be Every 10 Business Days, Every 30 Days, Every 5 Business Days, Next Day, or None. Otherwise, the following defaults may apply to the Reassessment Frequency field: When Plan Type is Problem List, the default Reassessment Frequency is blank; when Plan Type is Initial, the default Reassessment Frequency is Next Business Day; and, when Plan Type is Comprehensive, the default Reassessment Frequency is Every Five Business Days. In the Type drop-down menu 415, the user can select Comprehensive. The Reassessment Frequency may then update to Every 5 Business Days, and the Next Team Meeting date may automatically adjust to 5 business days in the future. In many embodiments, once the Comprehensive plan is signed, the system may automatically update the Type to Update, which requires the signature of all team members currently listed. Updates may be prompted for in a Notifications section or tab. In the Next Team Meeting section 420, the calendar icon can be clicked to select a date. In the open field 425 next to the Add Team Member button 430, the user can begin typing the first few letters of the team member the user wants to add, and then click the Add Team Member button 430. In the Comments box 435, the user can type any applicable notes, if needed. Finally, the user may click the OK button 440 at the bottom of the tasks tab 325 to complete the Treatment Plan. The user can then sign the Plan, which may create a Note in the main system and cause notifications to be sent to other co-signers for their signature.

VI. Treatment Plan Tasks

Various Treatment Plans tasks may be completed. For example, the following Treatment Plan tasks as described below: Editing Treatment Plan Information, Editing Patient-Specific Diagnostic Category Items, Adding Diagnostic Categories to the Treatment Plan, Creating New Diagnostic Category Items, Creating New Template Items, Creating Progress Notes, Creating Discharge Summary Notes, Signing Treatment Plans, Completing Treatment Plans, and Creating Templates (Security Key Holders Only).

Editing Treatment Plan Information:

The Treatment Plan information may be edited using the following steps. The Edit icon in the upper-left corner of the Treatment Plan tab 215 may be clicked. An Edit Plan menu may then open in the Tasks tab 325 on the left pane 210. The Type can be changed to the applicable type. The Reassessment Frequency may default to the applicable frequency and the Next Team Meeting calculates accordingly. In many embodiments, if the Reassessment Frequency is changed, the Next Team Meeting also recalculates. The user can change the date of the Next Team Meeting if desired (for example, if the team is unavailable on the scheduled date). Team members can be added. The user may type the first several letters of the name of the team member in the box 425 to the right of the Add Team Member Button 430. The team member's name may then appear in the Team Members list. In many embodiments, the listed team members may be the users who receive notifications for signing the current MDTP note, as well as notifications for the next team meeting. Finally, the user may click the OK button 440 at the bottom of the Tasks tab 325 when finished.

Figure 18:
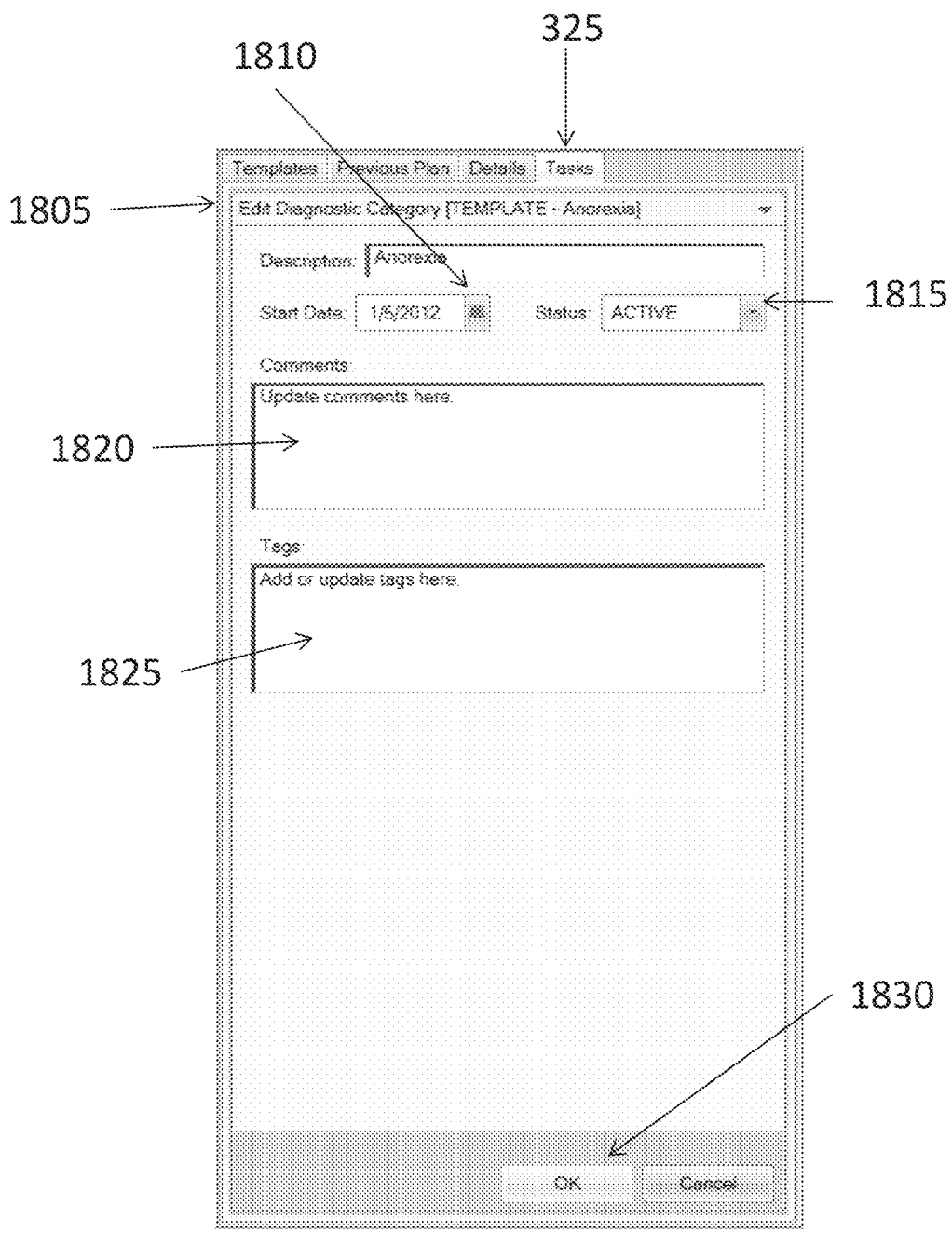
FIG. 18 shows a screenshot of a different portion of the MDTP application of FIG. 2 being used to update and edit patient-specific diagnostic category items.

Editing Patient-Specific Diagnostic Category Items:

Referring to FIG. 18, patient-specific Diagnostic Category items may be edited. In many embodiments, only users with the MDTP ADMIN key are allowed to edit template items. The following steps are for those users to edit patient-specific Diagnostic Category items. From the Templates tab 305, the user can click the Edit Icon next to the Problems 335, Recover Status 340, Objective 345, or Intervention 350 sections to edit. The Edit Diagnostic Category 1805 will then open in the Task tab 325. The user may click on the calendar icon 1810 or the status pull-down menu 1815 to update the Start Date and Status, as needed. In many embodiments, the Start Date defaults to the present date. The user can add or edit comments in the Comments box 1820 as needed. The user can add or edit comments in the Tags box 1825 as needed. When finished, the user can click the OK button 1830 at the bottom of the Tasks tab.

Figure 19:
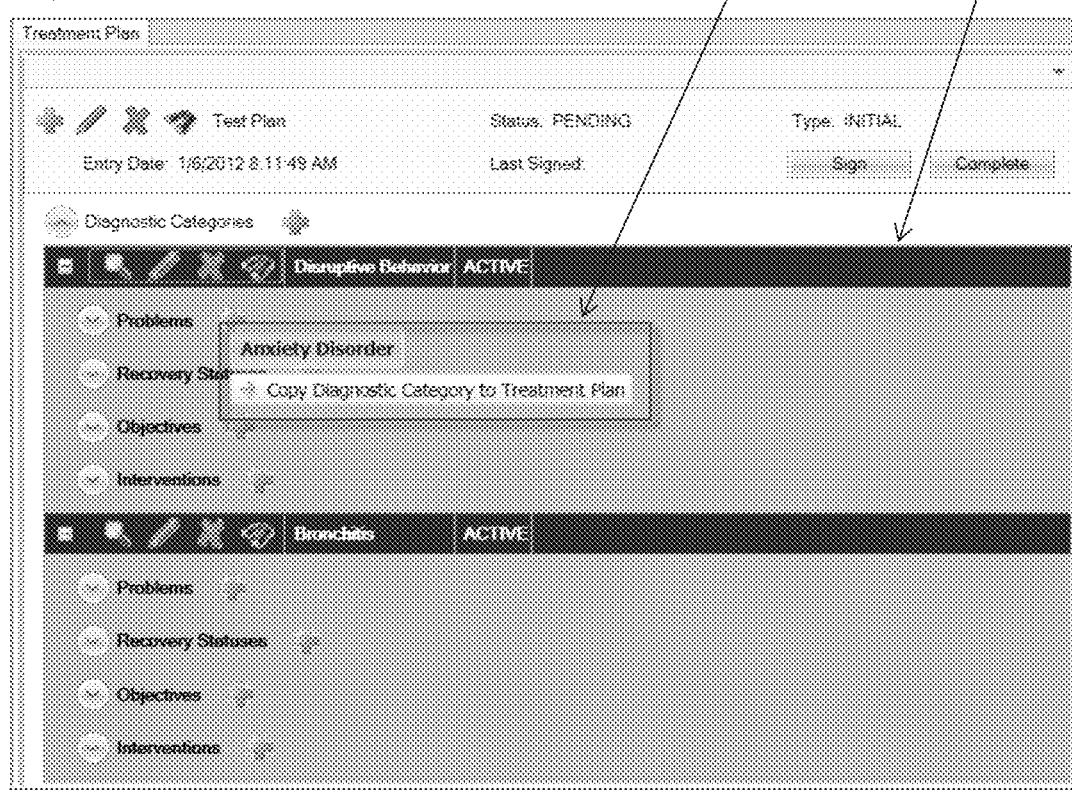
FIG. 19 shows a screenshot of a different portion of the MDTP application of FIG. 2 being used to add diagnostic categories to a treatment plan.

Adding Diagnostic Categories to the Treatment Plan:

Items may be added one at a time or in multiples to the patient's Treatment plan. Referring back to FIG. 4, from the Templates tab 305, the user can select the Diagnostic Categories 330 that apply to each diagnosis for the patient. To filter the list of times, the user can type one or more terms, separated by commas, which may be associated with the item, such as Anxiety, in the Search field 310 at the top of the Templates tab 305, and then press Enter. The list may then filter with the user selected item(s) at the top. In many embodiments, the user can select multiple items by holding down the Ctrl key and clicking the desired items. As shown in FIG. 19, the user can drag and drop the items, for Anxiety Disorder 1905, to the blue section 510 of the Treatment Plan tab 215.

Figure 20:
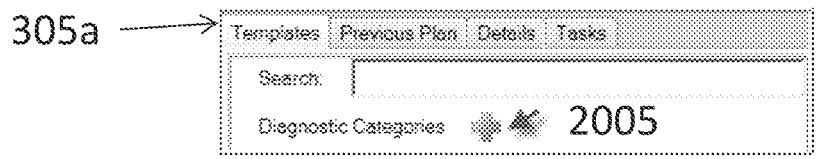
FIGS. 20, 21, and 22 show screenshots of different portions of the MDTP application of FIG. 2 being used to create new diagnostic category items.
Figure 21:
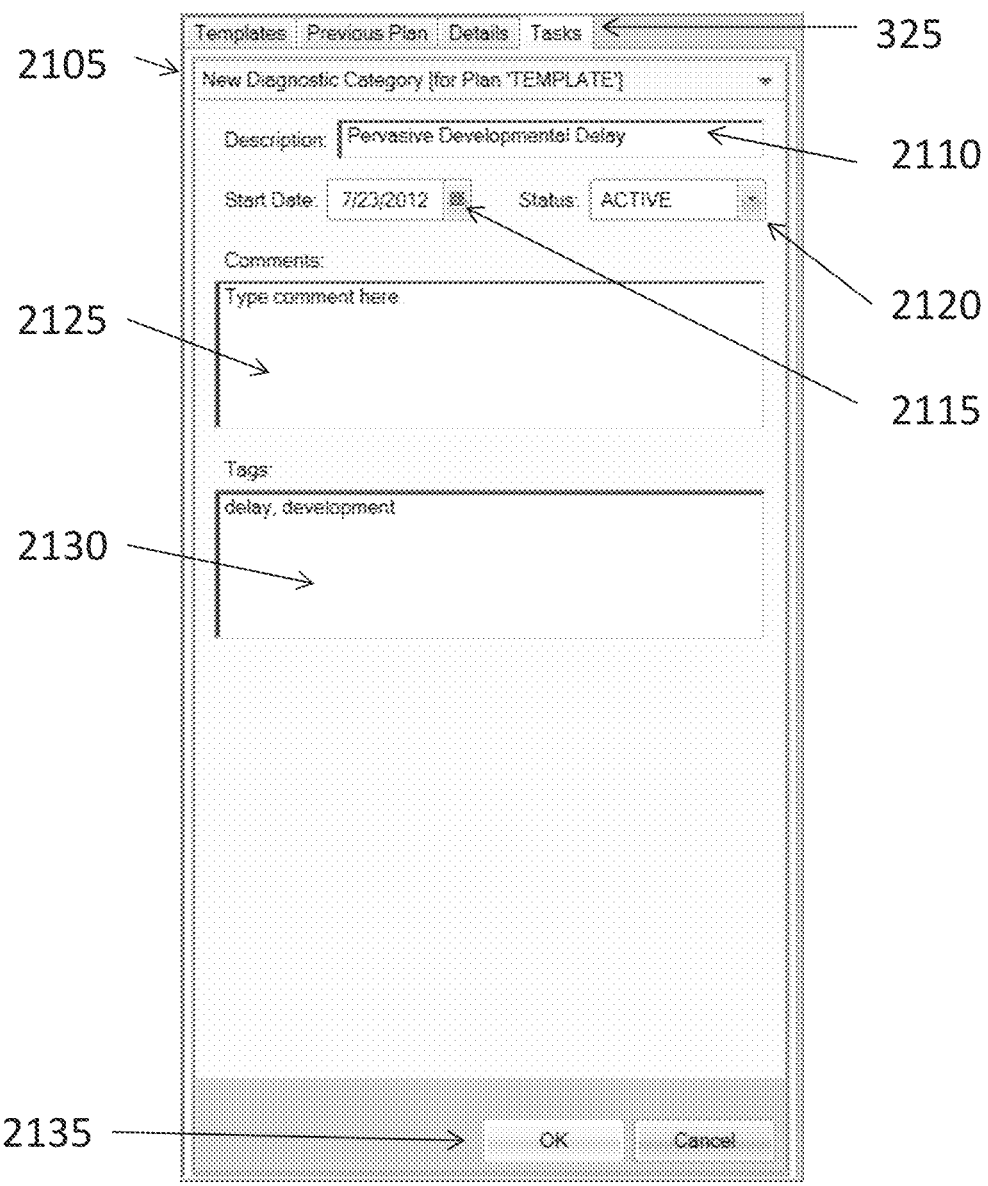
Figure 22:
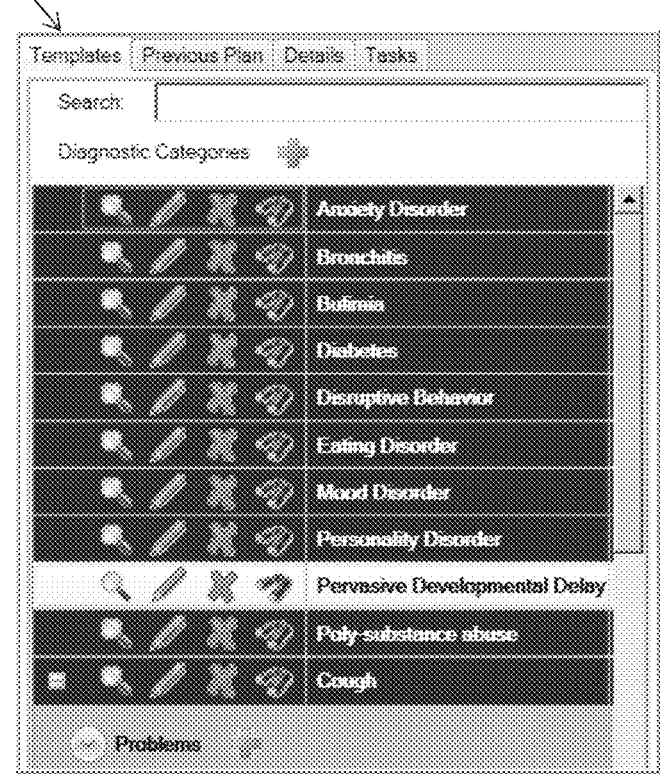

Creating New Diagnostic Category Items:

Referring to FIGS. 20, 21, and 22, the user can create a new Diagnostic Category item if the one the user needs does not exist in the site-defined list. As shown in FIG. 20, from the relevant portion 305a of the Templates tab, the Add New Diagnostic Categories icon 2005 can be clicked below the search field 310. This will open the Task tab 325 with a blank New Diagnostic Category 2105, for example, for Plan 'TEMPLATE'. In the Description box 2110, a name can be typed for the new Problem, Recovery Status, Objective, or Intervention item. In this example, "Pervasive Developmental Delay" is used. If needed, in the Start Date field, the user can type a date or click the calendar icon 2115 to select a date. In the Status pull-down menu 2120, the applicable status can be selected. Active is the default selection. In the Comments box 2125, the user can type any applicable comments. In the Tags box 2130, any applicable tag terms can be entered. The OK button 2135 can then be clicked and the new Diagnostic Category may appear in the Templates tab 305 as shown by FIG. 22.

Figure 23:
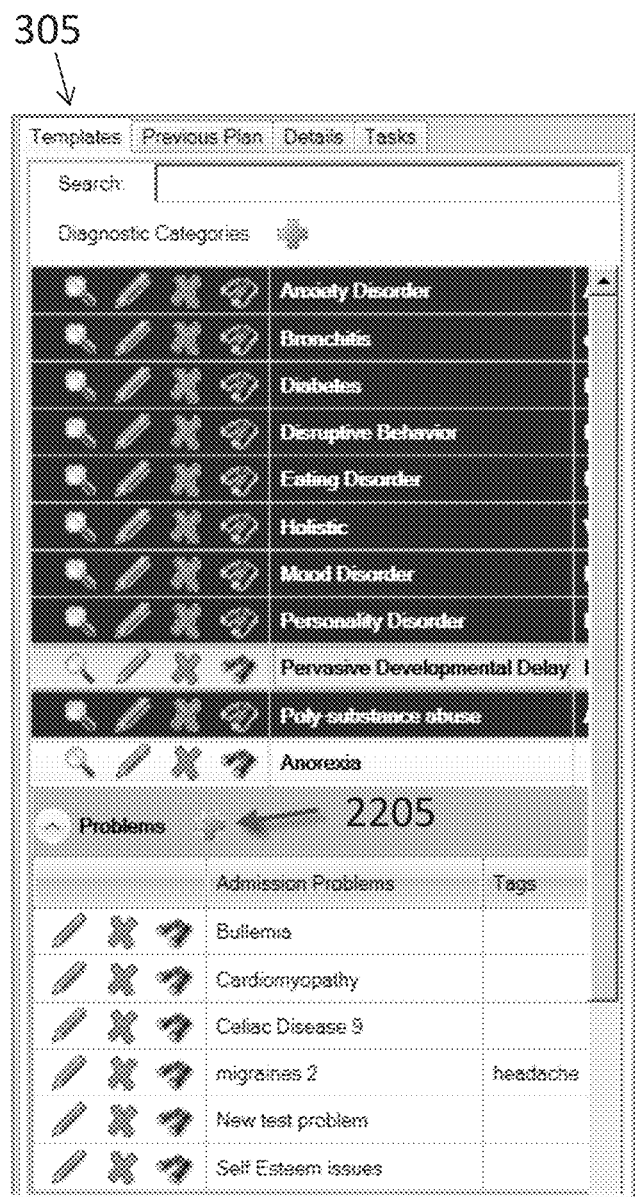
FIGS. 23, 24, and 25 show screenshots of different portions of the MDTP application of FIG. 2 being used to create new template items.
Figure 24:
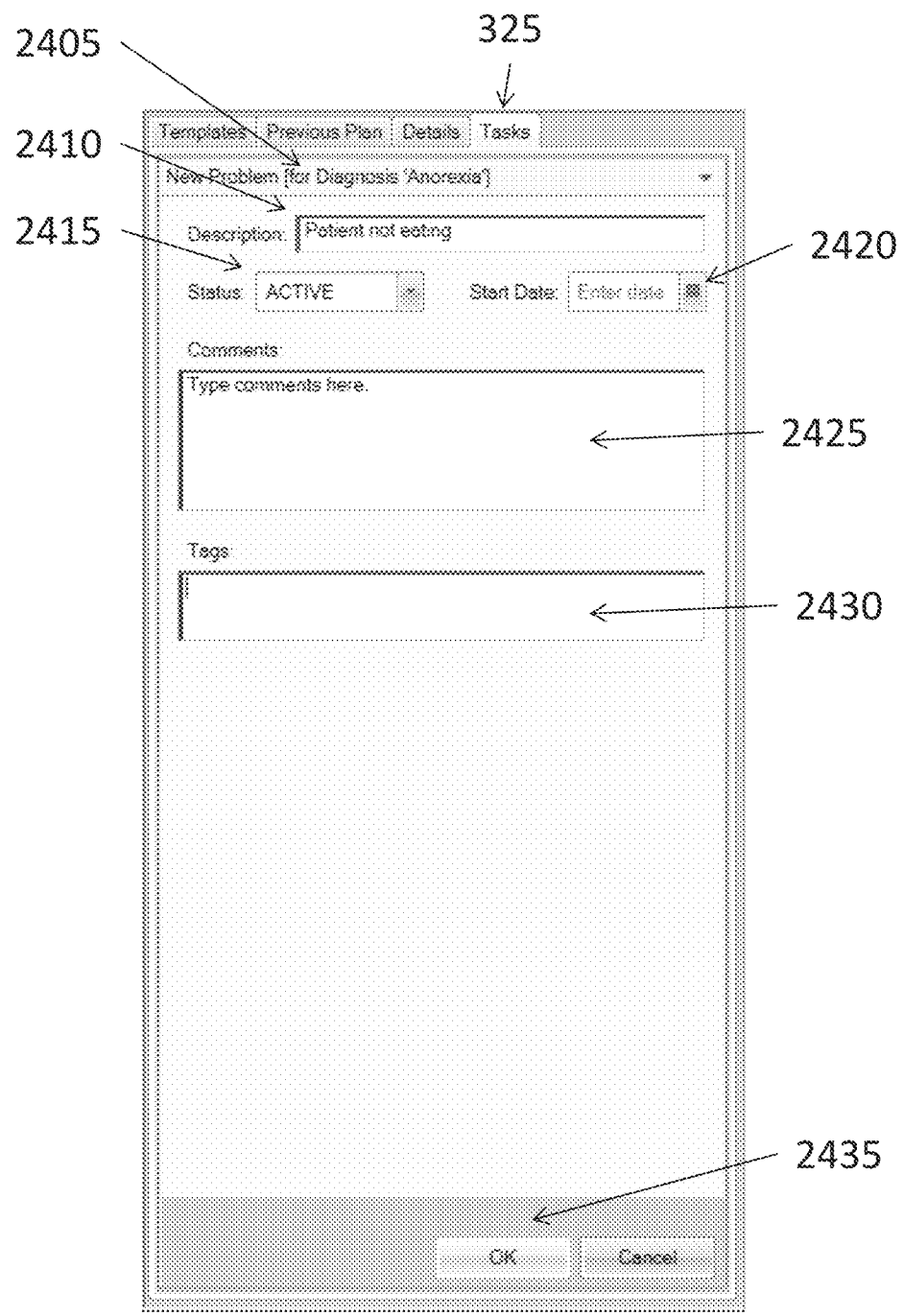
Figure 25:
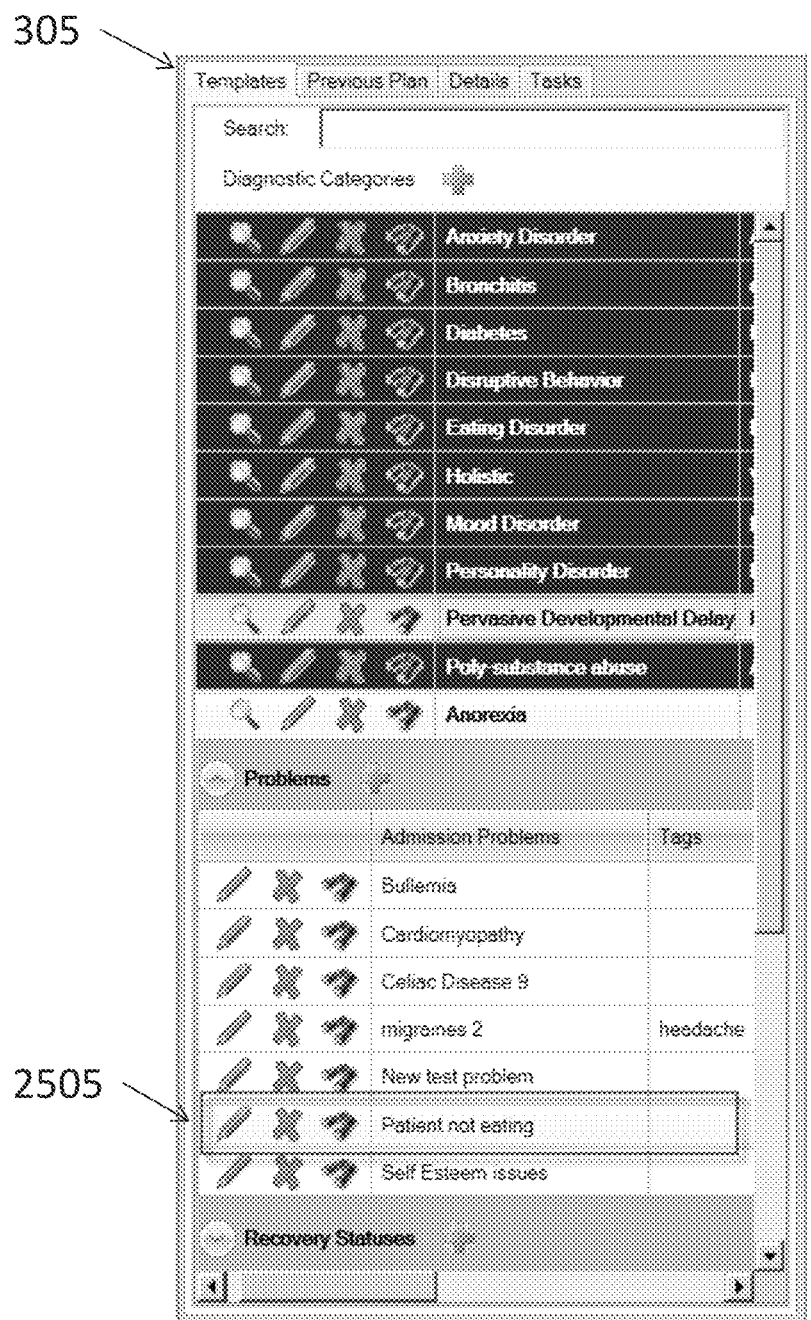

Creating New Template Items:

Referring to FIGS. 23, 24, and 25, the user can create a new Template item in the MDTP. Users who hold the MDTP ADMIN key can create a new Problem, Recovery Status, Objective, or Intervention if one does not exist in the Templates list. From the Templates tab 305, the Add icon 2205 next to the Problem, Recovery Status, Objective, or Intervention for which the user wants to create a new item can be clicked. As shown in FIG. 24, the Tasks tab 325 then opens for the New Problem 2405, for example, for Diagnosis 'Anorexia'. In the Description Field 2410, the user can type a description for the new Problem. In the Status pull-down menu 2415, the applicable status can be selected from the drop-down menu. The applicable status may be Active, Inactive, or Resolved. In the Start Date section, the user can type in a date or click the calendar icon 2420 to select a date. In the Comments box 2425, the user can type in any applicable notes. In the Tags box 2430, the user can type in any applicable tags. The OK button 2435 can be clicked at the bottom of the Tasks tab 325 and the new Problem 2505 may then appear in the list of Problems in the Templates tab 305 as shown in FIG. 25.

Creating Progress Notes:

Various progress notes can be created. An MDTP Note document can be created and updated at each revision of the MDTP plan. Progress Notes can be written by each individual member of the team in the Notes component. Intervention items for their discipline can comprise objects that can be pulled into their note and that the individuals can document progress on.

Similarly to the other Treatment Plan tasks described above, the user can create MDTP notes. Progress Notes for Problems indicate the patient's progress. The MDTP Progress Notes can be imported to a more general application, such as main system 100, when the Plan is signed. Referring back to FIG. 3, from the Treatment Plan pane 215, the user can click the Edit icon 365 next to the Problem for which the user wants to create a note. The Edit Problem pane then opens in the Tasks tab 325. Status and Start Date can be updated as needed similarly to that described above. Any notes and comments can be typed in Comments and Tags box, respectively, similarly to that described above. An OK Button can be clicked similarly to that described above; and, from the Treatment Plan pane 215, the user can sign the plan which then imports a Progress Note to the more general application.

Creating Discharge Summary Notes:

Similarly to the other Treatment Plan tasks described above, the user can create discharge summary notes. Discharge Summary Notes indicate the patient's discharge status and are imported to a more general application when the Plan is signed. The Discharge Summary Notes include Problems, Discharge Goals, and the first and lasts Scale scores. Referring back to FIG. 3, from the Treatment Plan pane 215, the user can click the Edit icon 365 next to the Problem or Recovery Status, or for which the user wants to create a note. The Edit Problem or Edit Recovery Status pane will then open in the Tasks tab 325. The Status and Start Date can be updated as need similarly to that described above. An Include Scale check box can be selected to select a scale measure similarly to that described above. Any notes can be entered in the Progress Comments field and any tags can be entered in the Tags field. An OK Button can be clicked similarly to that described above; and, from the Treatment plan pane 215, the user can sign the plan which then imports a Discharge Summary Note to the more general application.

Figure 26:

Signing Treatment Plans:

Referring now to FIGS. 26 and 27, after the Treatment Plan has been updated, a Team Member can initiate the signing process by signing the Treatment Plan, which then creates an MDTP Note. The user can click the Sign button 2605 at the bottom of the relevant portion 215f of the Treatment Plan tab 215. A Sign Plan (draft of the MDTP Note) summary may then appear in the Tasks tab 325. In many embodiments, there are mandatory items that must be addressed prior to signing, and the user may be given a preview at the top of the Note that they can then sign. Typically, the note cannot be changed at this point, although a team member may create an Addendum MDTP Note with changes, if necessary. Generally, the following items must be complete prior to signing, for all Plan types: Diagnosis Status, Problem Status, Objective Status, Intervention Care Action, and Objective Progress Comments when the Plan Type is Update. The user can then review the Sign Plan (Note) 2710 and if everything is correct, electronically sign the Note by typing his signature code in the Signature field 2715 at the bottom of the Tasks tab 325, and then click an Ok button 2720. This creates an MDTP note, which is accessible from the Notes tab in the main system 100 and sends notifications for signature for signature to all members listed currently as Team Members. Generally, no further notifications are sent once a Treatment Plan is signed. The next time the Treatment Plan is opened, the status can show as Signed and may default to Update. In many embodiments, if a new Treatment Plan is created, all previously identified team members involved in the update and review of the previous plan can be pulled into the new plan and receive an e-mail notification for a plan review when a subsequent plan review is scheduled.

Figure 28:
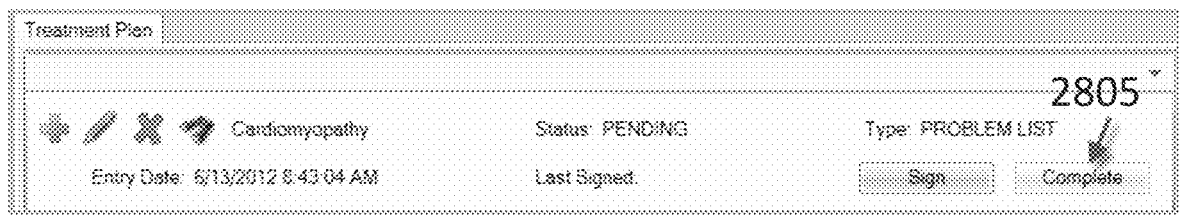
FIG. 28 shows a screenshot of a portion of the MDTP application of FIG. 2 being used to mark a treatment plan as complete.

Completing Treatment Plans:

Referring now to FIG. 28, the same items that are required and functions that occur when a Plan is signed apply to completing the Plan. However, the user clicks the Complete button 2805 to close out the Plan to further changes.

Figure 29:
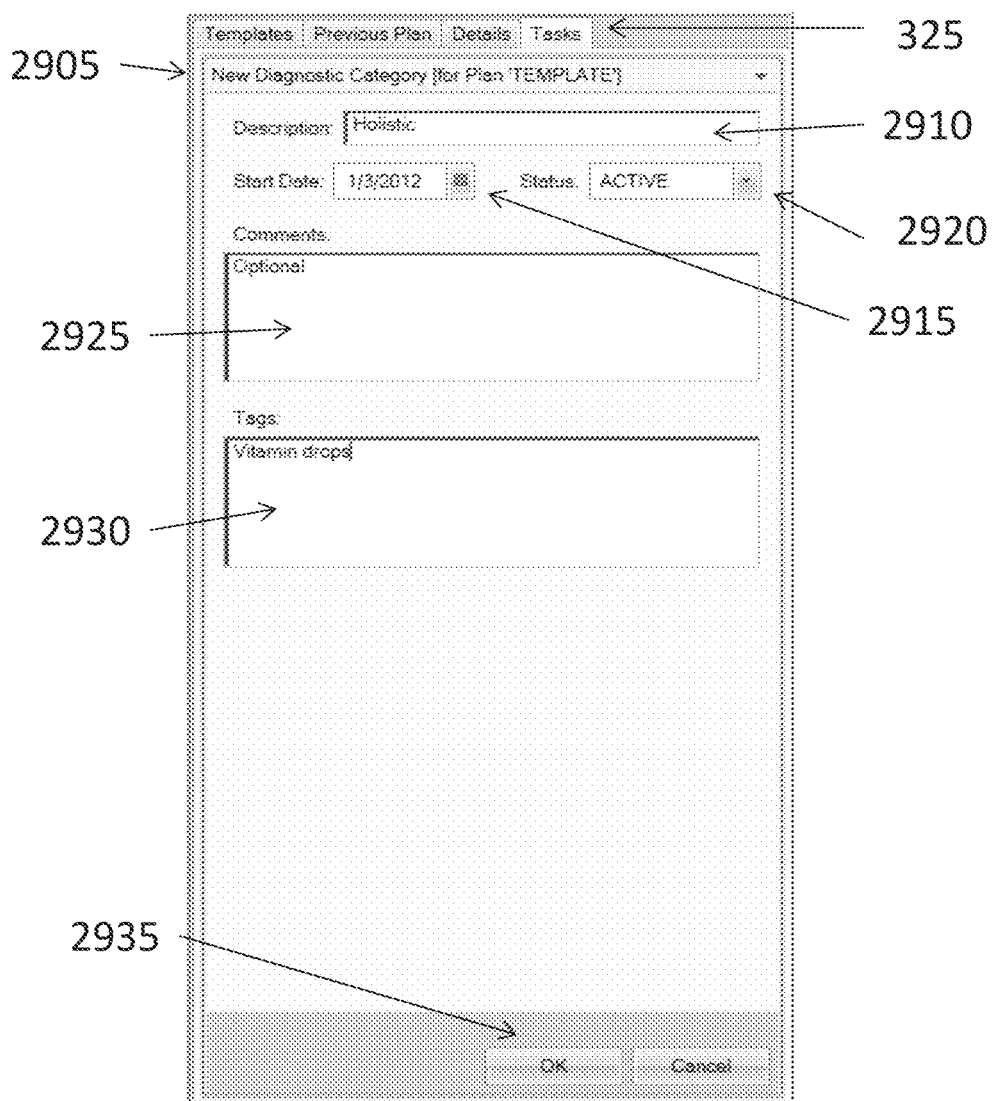
FIG. 29 shows a screenshot of a portion of the MDTP application of FIG. 2 being used create a new template or diagnostic category.

Creating Templates (Security Key Holders Only):

Referring now to FIG. 29, the user can create new Templates or Diagnostic Categories if one template does not exists. In many embodiments, only MDTP administrators who hold a specified Security Key can create templates. In the Templates tab 303, the Add icon 250 next to the Diagnostic Category can be clicked. A New Diagnostic Category 2905, for the Plan 'TEMPLATE', then opens in the Tasks tab 325. In the Description box 2910, a name can be entered for the new template. In the example of FIG. 29, the name Holistic is used. In the Start Date section, the user can enter a date or click the calendar icon 2915 to select a date. In the Status pull-down menu 2920, the user can select Active from the drop-down menu. If deactivating a Template, the user can select Inactive or Resolved. In the Comments box 2925, the user can enter a note if needed. Typically, this field is optional. In the Tags box 2930, the user can enter any tags the user may want to associate with the new Template. In the example of FIG. 29, the tag "Vitamin drops" was used. After the Template is created, when in the Templates tab 305, the user can then type the first few letters (or the entire word) of the tag(s) and after pressing Enter, the appropriate item (Holistic, in the example of FIG. 29) shows at the top of the Diagnostic Categories list. The OK button 2935 can be clicked at the bottom of the Tasks 325 pane to create the new Diagnostic Category.

VII. Example of MDTP Implementation

FIG. 1 shows a flowchart of a workflow process 3000 that can be used with the MDTP application described herein. In a step 3010, a doctor or MD creates MDTP problems and diagnoses at the admission of a patient. In a step 3020, a nurse creates an initial plan which is typically multi-disciplinary, involves multiple team members, and includes initial interventions. In a step 3030, within X hours, the MDTP team collaborates on an initial plan, including developing the list of problems, recovery statuses, and objectives. In a step 3040, each of the team members enters their interventions and the team agrees and signs. In a step 3050, the MDTP application prompts updates for every Y days until discharge. In a step 3060, the team collaborates on updates to the problems, recovery statuses, and objectives. In a step 3070, each team member enters their interventions, the team agrees on progress and changes, and the team signs. Steps 3060 and 3070 may be repeated until discharge.

FIGS. 31 to 49 show screenshots of the MDTP application described herein in use to create and implement an exemplary treatment plan. Many of the steps and system features described with reference to FIGS. 31 to 49 below are similar to the steps and system features described above.

Figure 31:
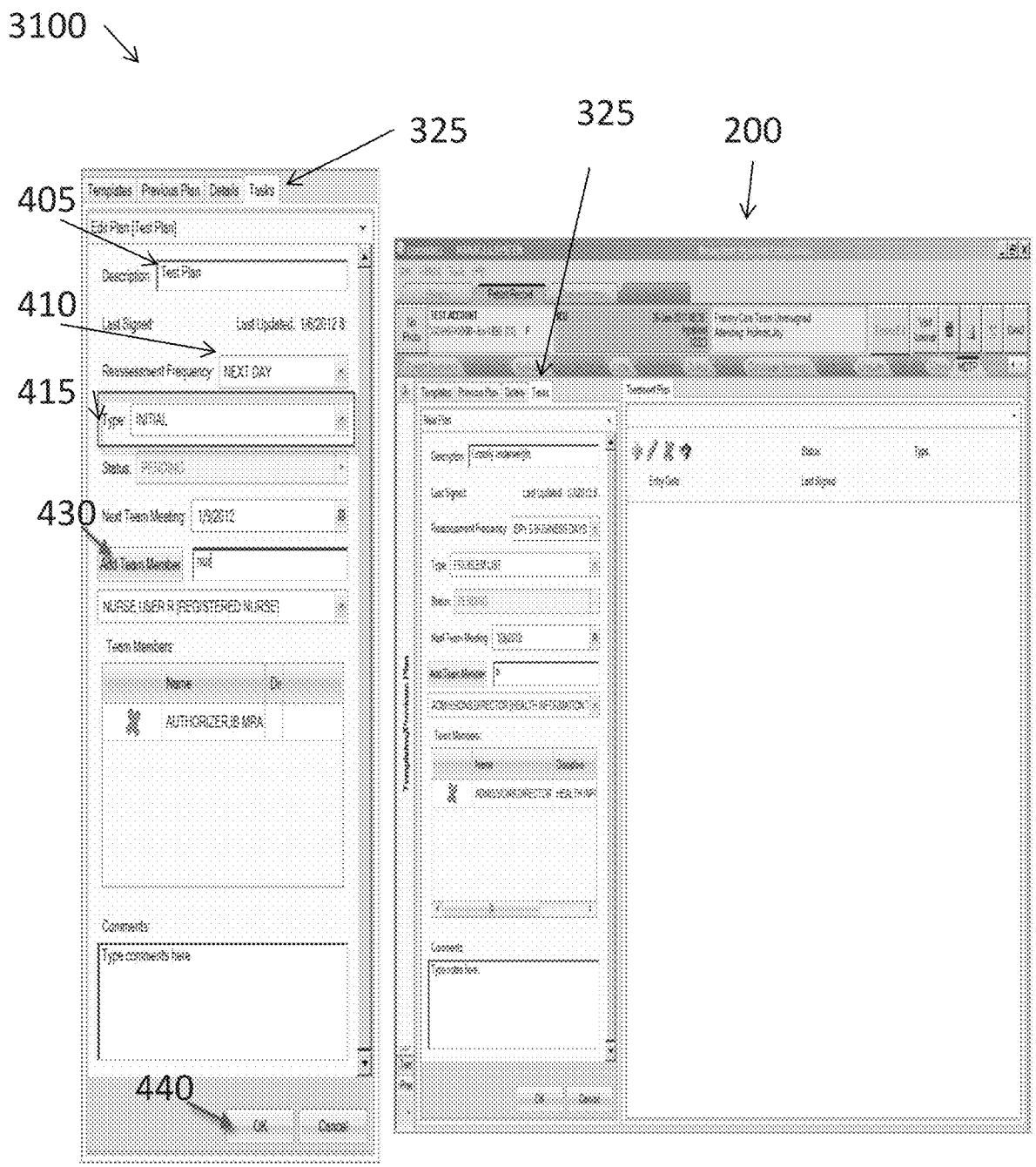

An initial MDTP plan is first created. As shown in FIG. 31, in a step 3100, when a MDTP is established, the user names the plan through the description field 405 in tasks pane 325, sets the reassessment frequency through the reassessment frequency drop down menu 410 which usually defaults to the site standard, and the type of plan is set, e.g., problem list entry, initial, comprehensive, or update, through the type drop-down menu 415. Team members may be added with add team member button 430 and the initial MDTP plan can be set by clicking OK button 440.

Figure 32:
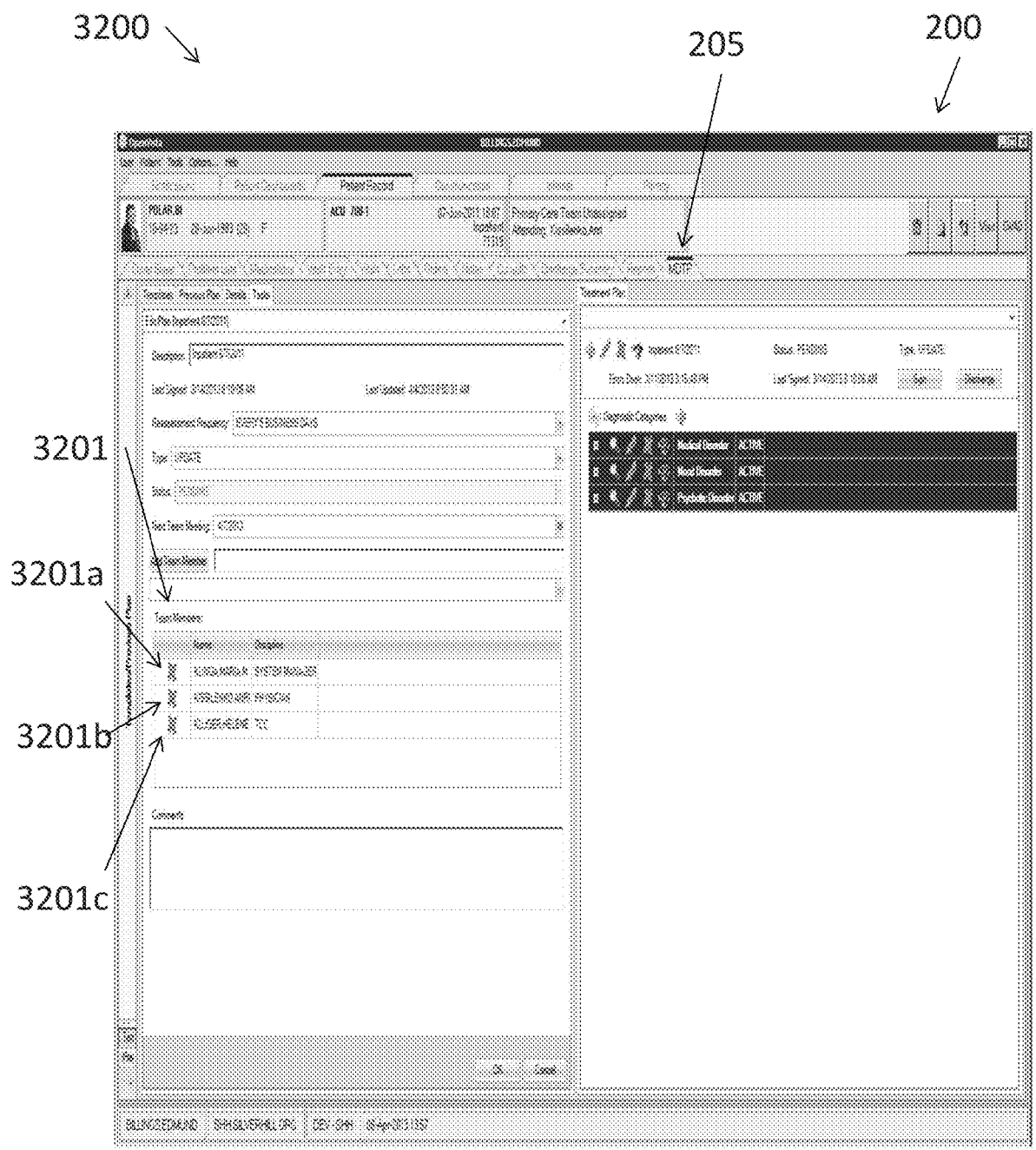
Figure 33:
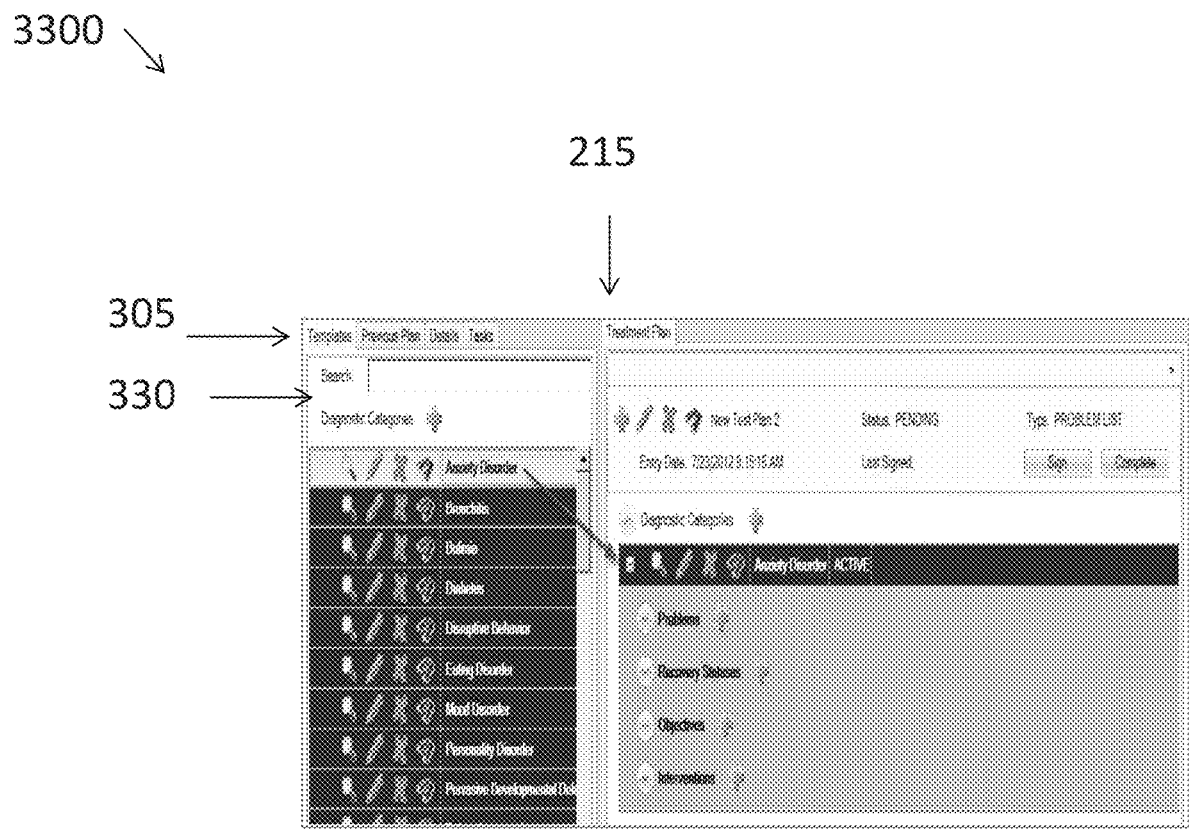
Figure 34:
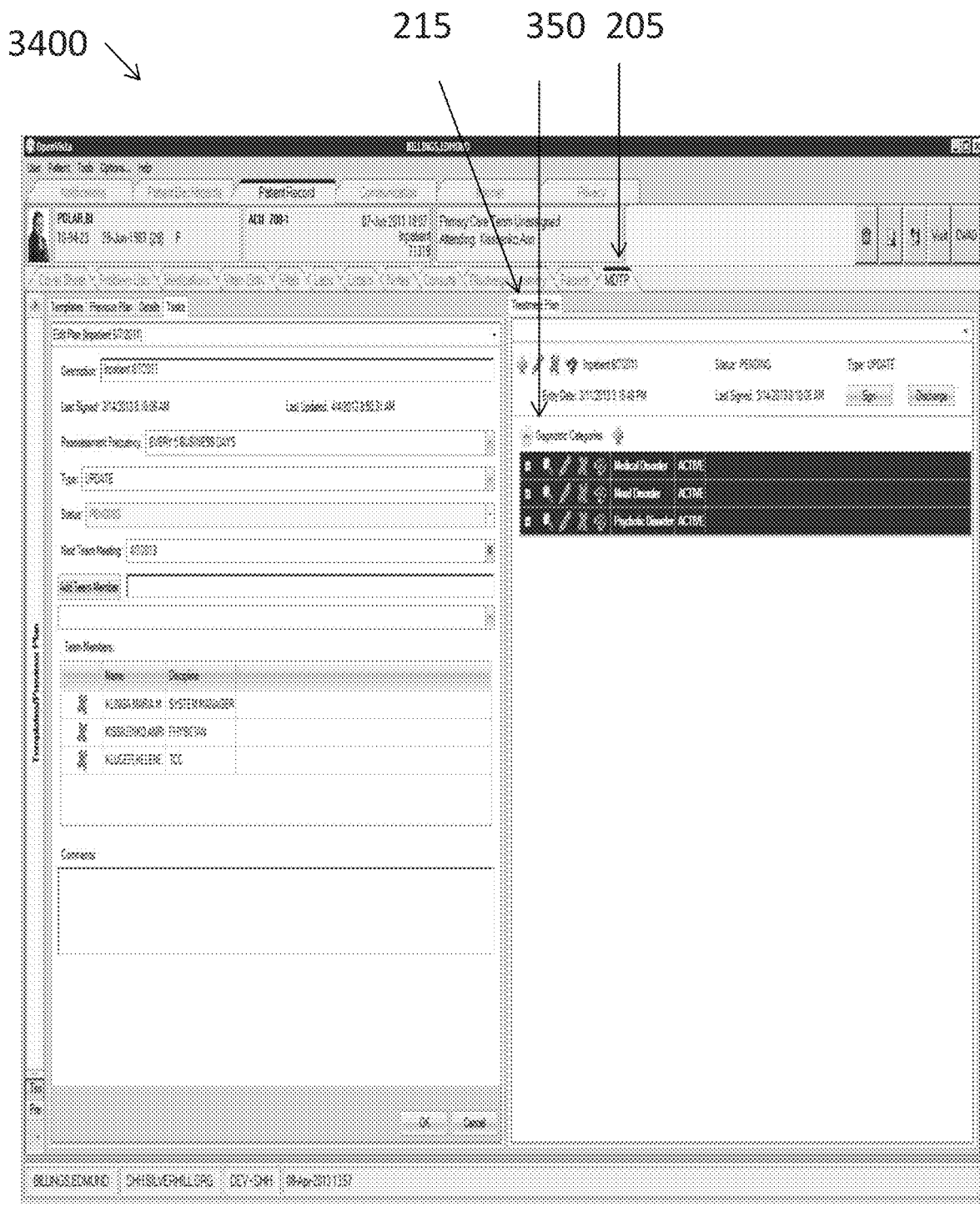

A physician enters diagnoses for the initial MDTP plan. As shown in FIG. 32, in a step 3200, a treatment plan is created and a multi-disciplinary team 3201 is defined. Each team member will be notified when updates are required and can document their interventions in progress notes. In the example shown by FIG. 32, the team members of the multi-disciplinary team 3201 include a system manager 3201a, a physician 3201b, and a social worker 3201c. As shown in FIG. 33, in a step 3300, the physician establishes the initial problem list as a basis of the MDTP plan and enters diagnoses from the templates tab 305 of diagnostic categories 330 into the treatment plan pane 215. As shown in FIG. 34, in a step 3400, the physician creates the initial plan in the treatment plan pane 215 and enters the diagnoses as diagnostic categories in the diagnostic category menu 330 of the MDTP pane 205.

Figure 35:
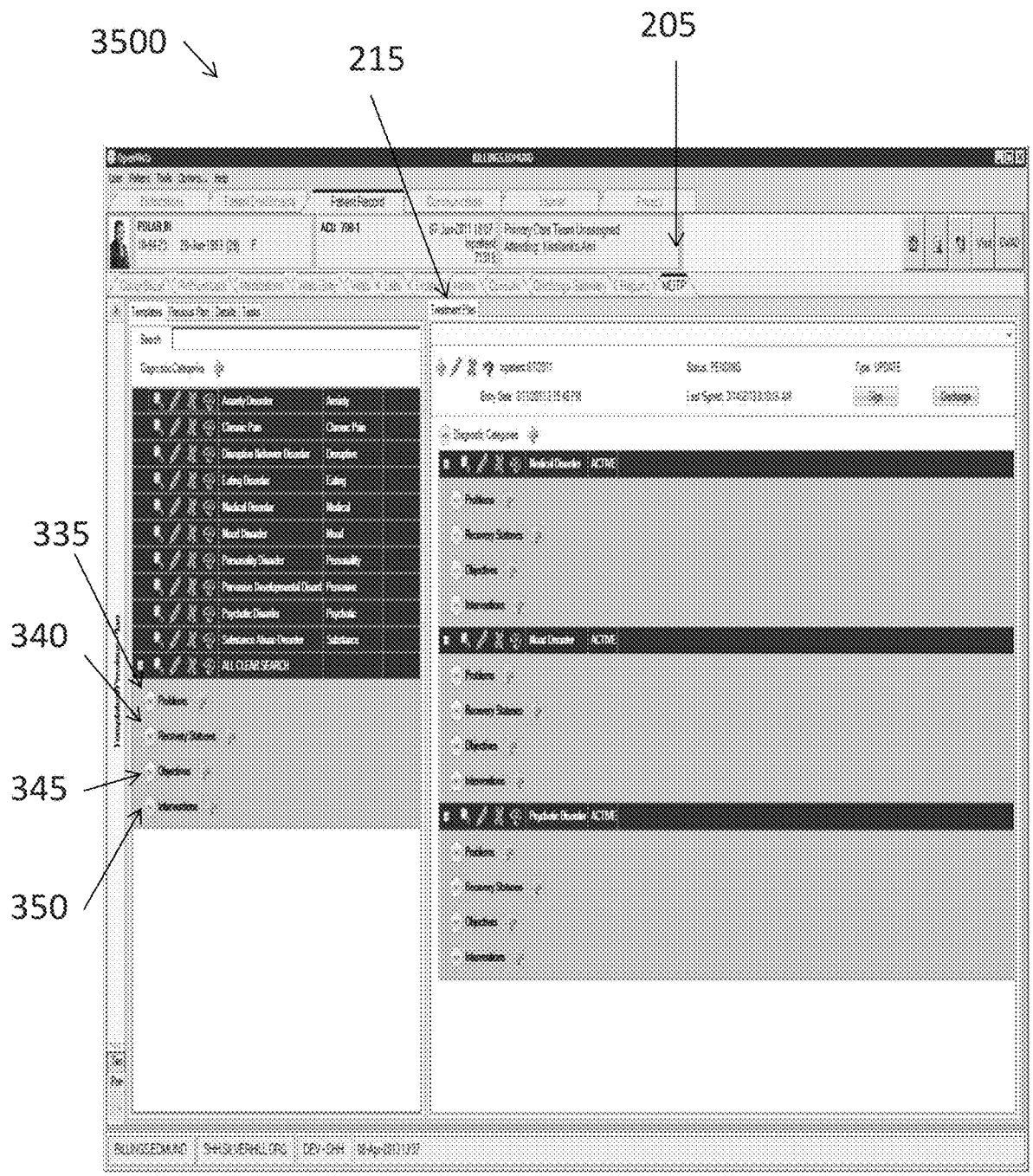
Figure 36:
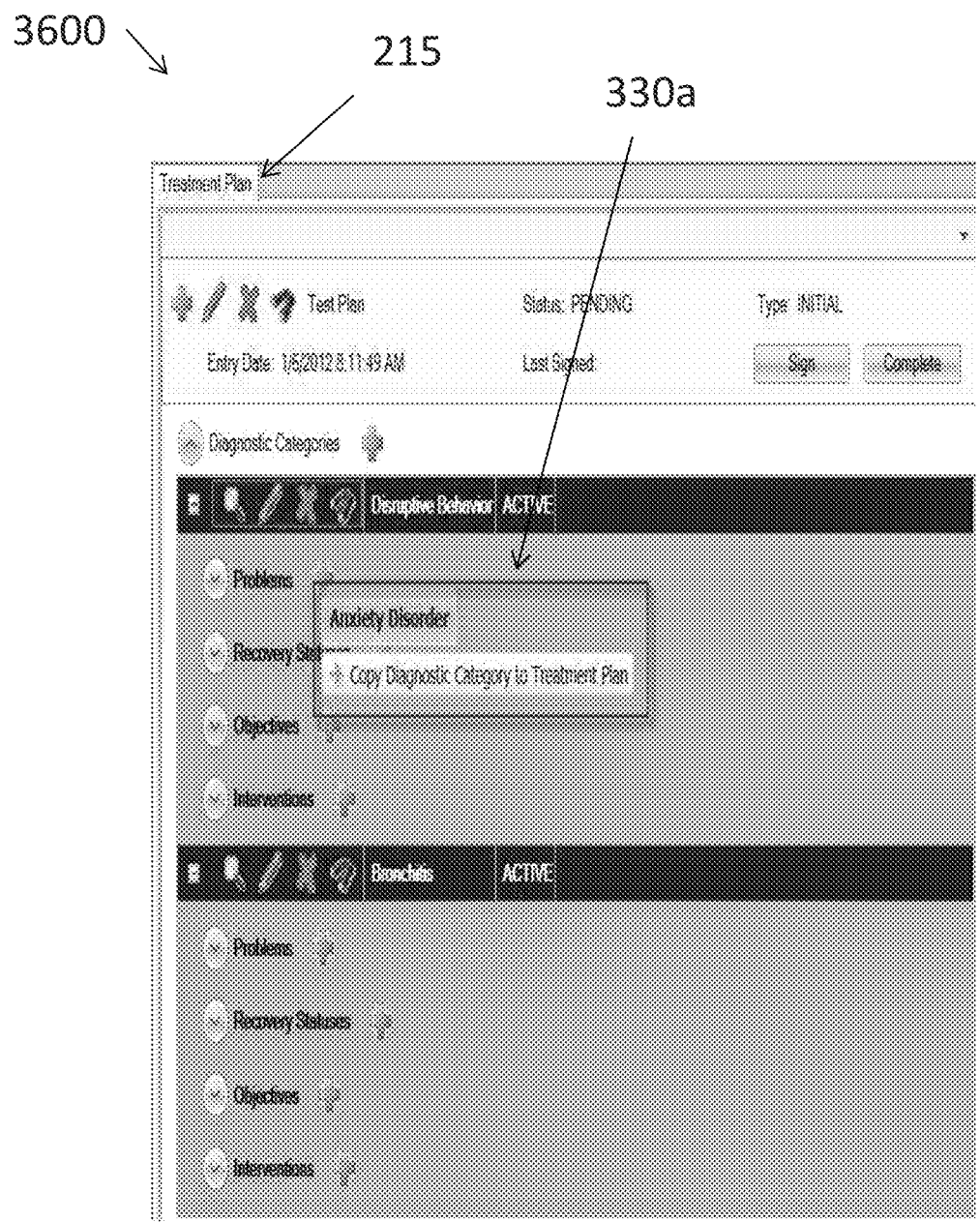

A comprehensive MDTP is then created. As shown in FIG. 35, in a step 3500, the multi-disciplinary team 3201 meets in conference where each member of the tem can place problems 335, recovery statuses 340, objectives 345, and interventions 350 into the plan shown by the MDTP pane 205. The entire team 3201 can see the plan as it is being built. The building of the plan occurs during the team's collaborative discussion. The plan is created, for example, by dragging and dropping entries 330a into the treatment plan tab 215 of the MDTP pane 205 in a step 3600 as shown by FIG. 36.

Figure 37:
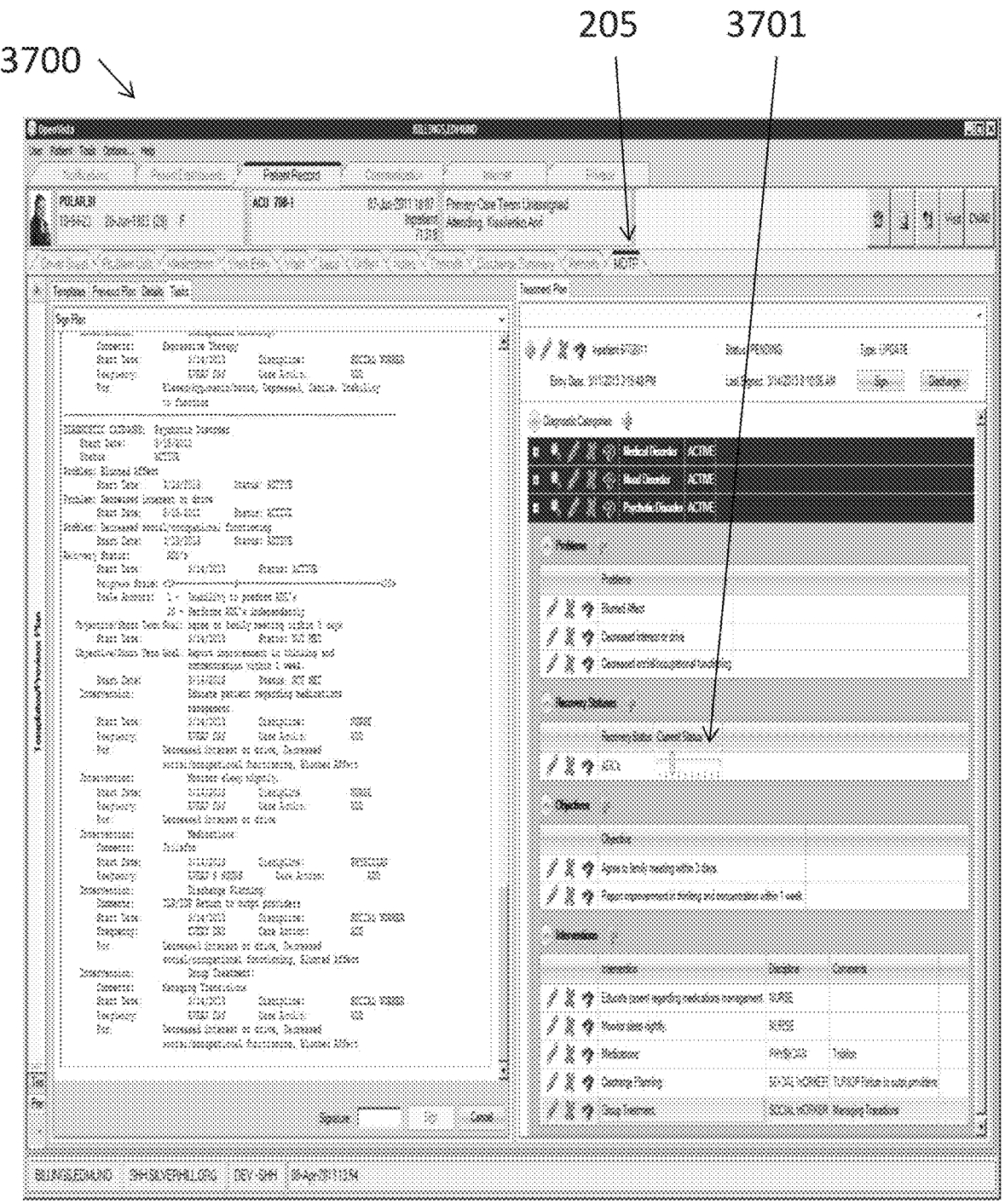
Figure 38:
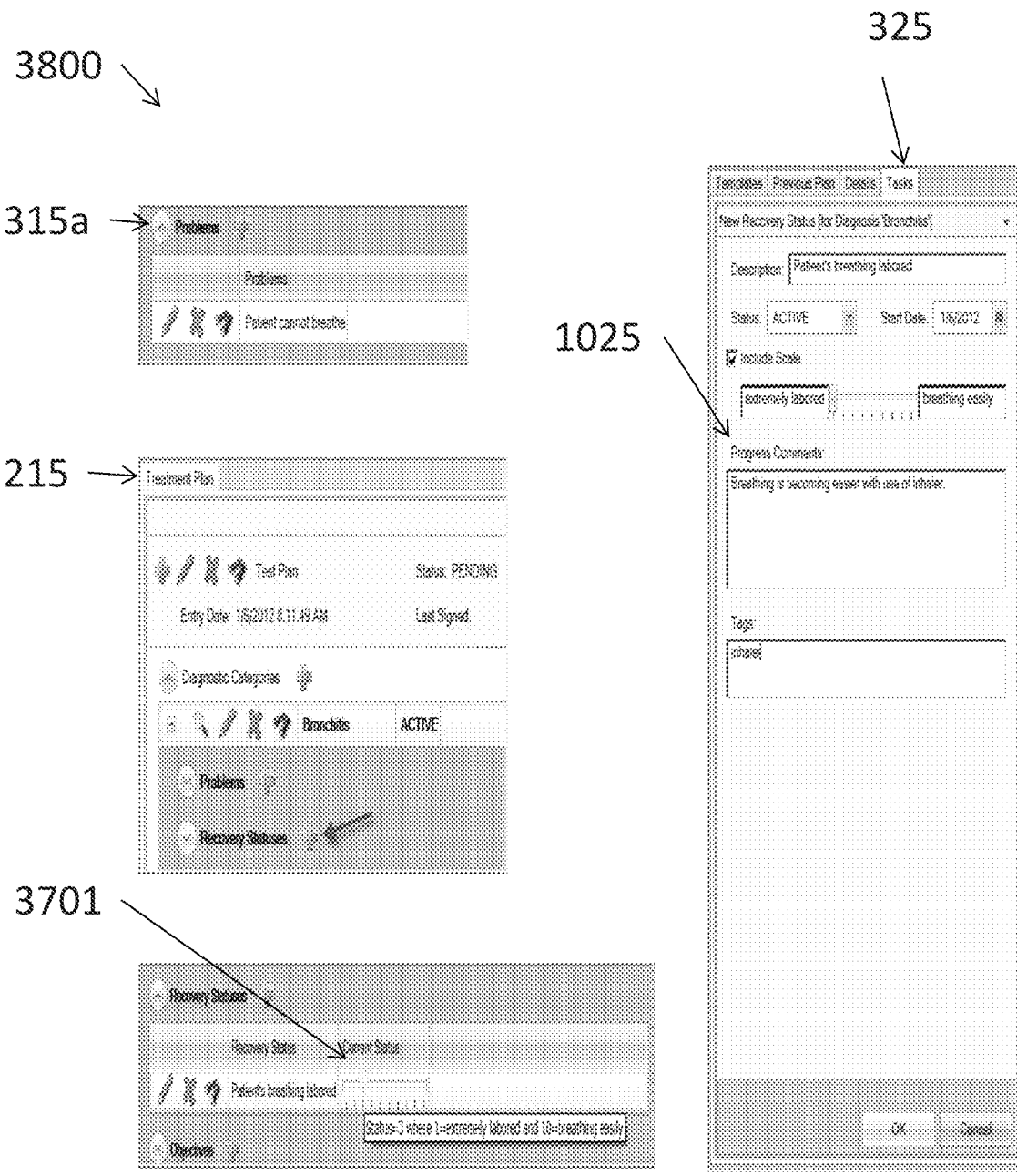

As shown in FIG. 37, in a step 3700, progress is made toward one or more recovery statuses. The recovery statuses section of the treatment plan tab 215 has a progress meter 3701 on a ligand scale for the tracking and documentation of progress toward recovery. The team 3201 can have a shared goal and monitor their collaborative progress toward it. An example of a recovery status is shown in FIG. 38 as a step 3800. In the step 3800, if the patient feels difficulty breathing, a recovery status is entered, the scale 3701 can be defined from labored breathing to breathing easily, and progress comments can be entered in comments box 1025 of the task tab 325, e.g., as "Breathing is becoming easier with the use of inhaler" as shown in FIG. 38.

Figure 39:
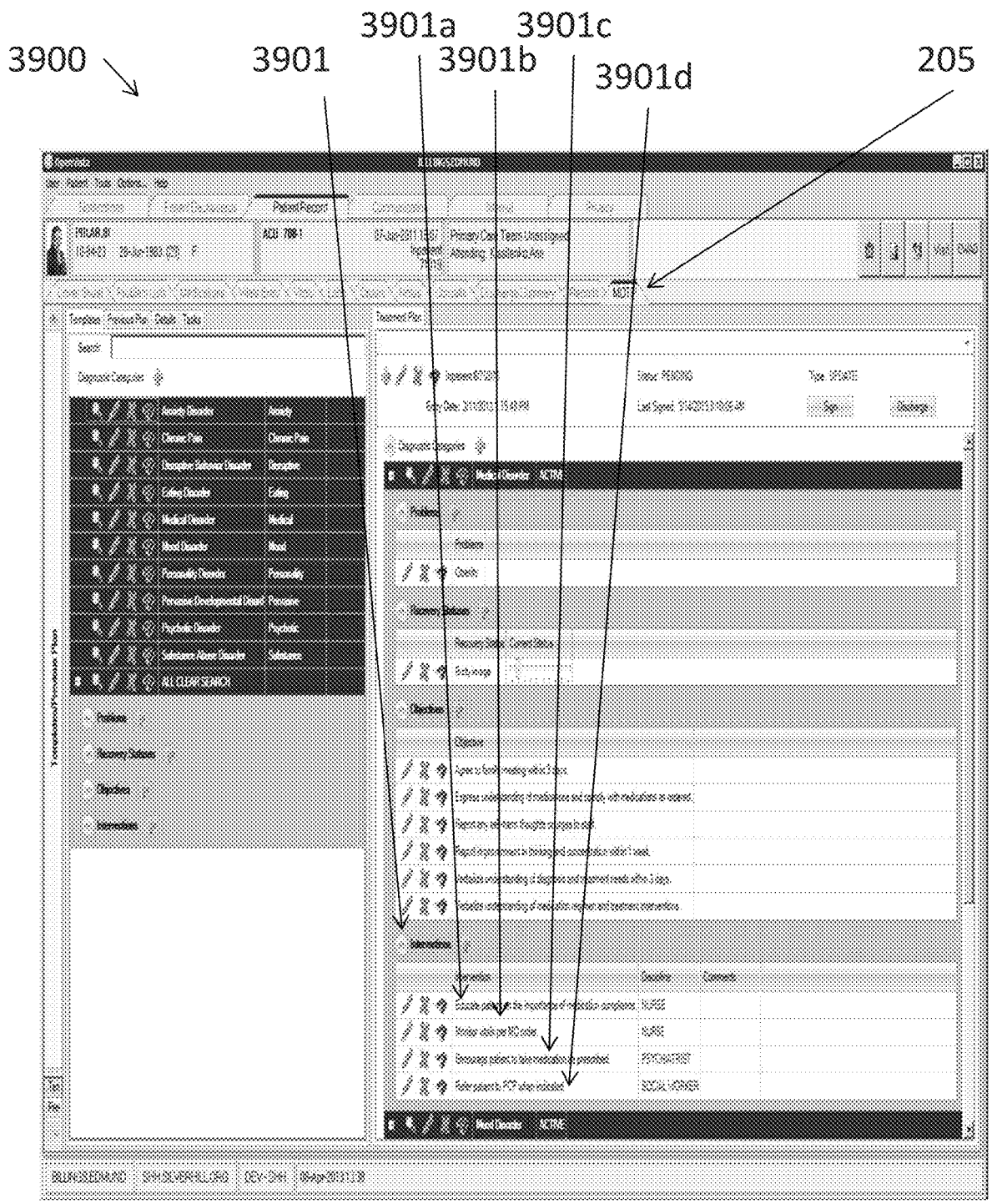
Figure 40:
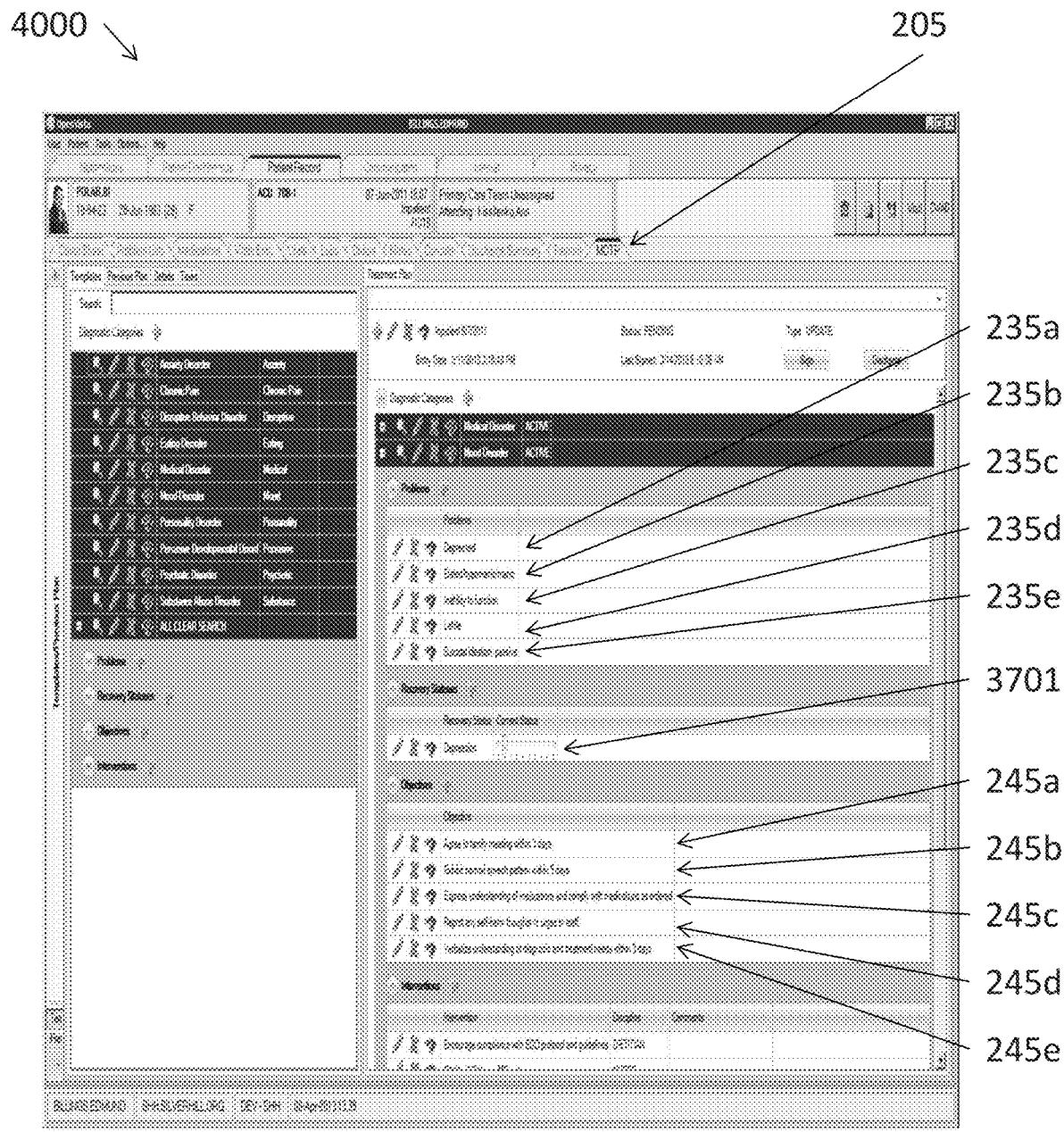
Figure 41:
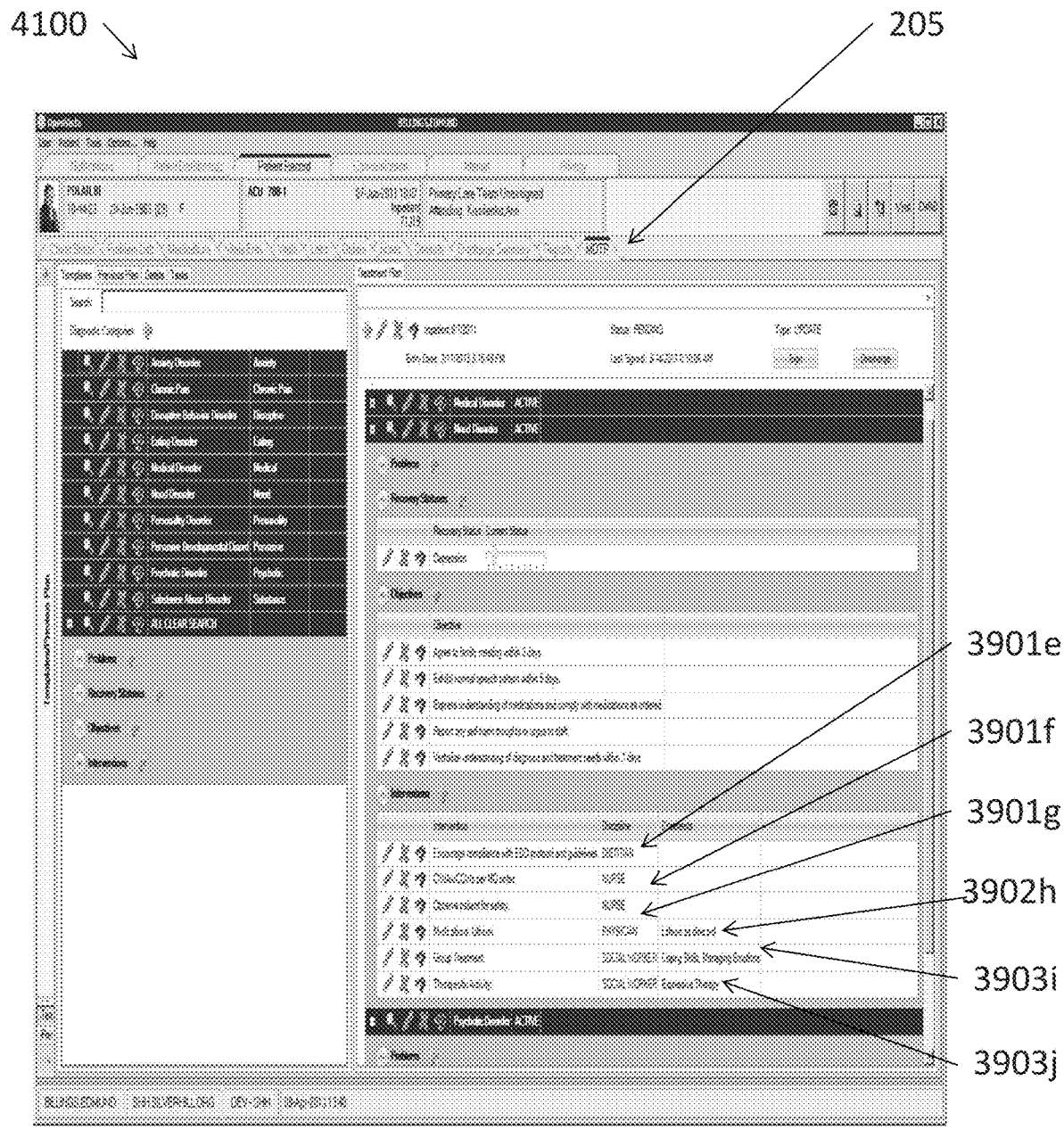
Figure 42:
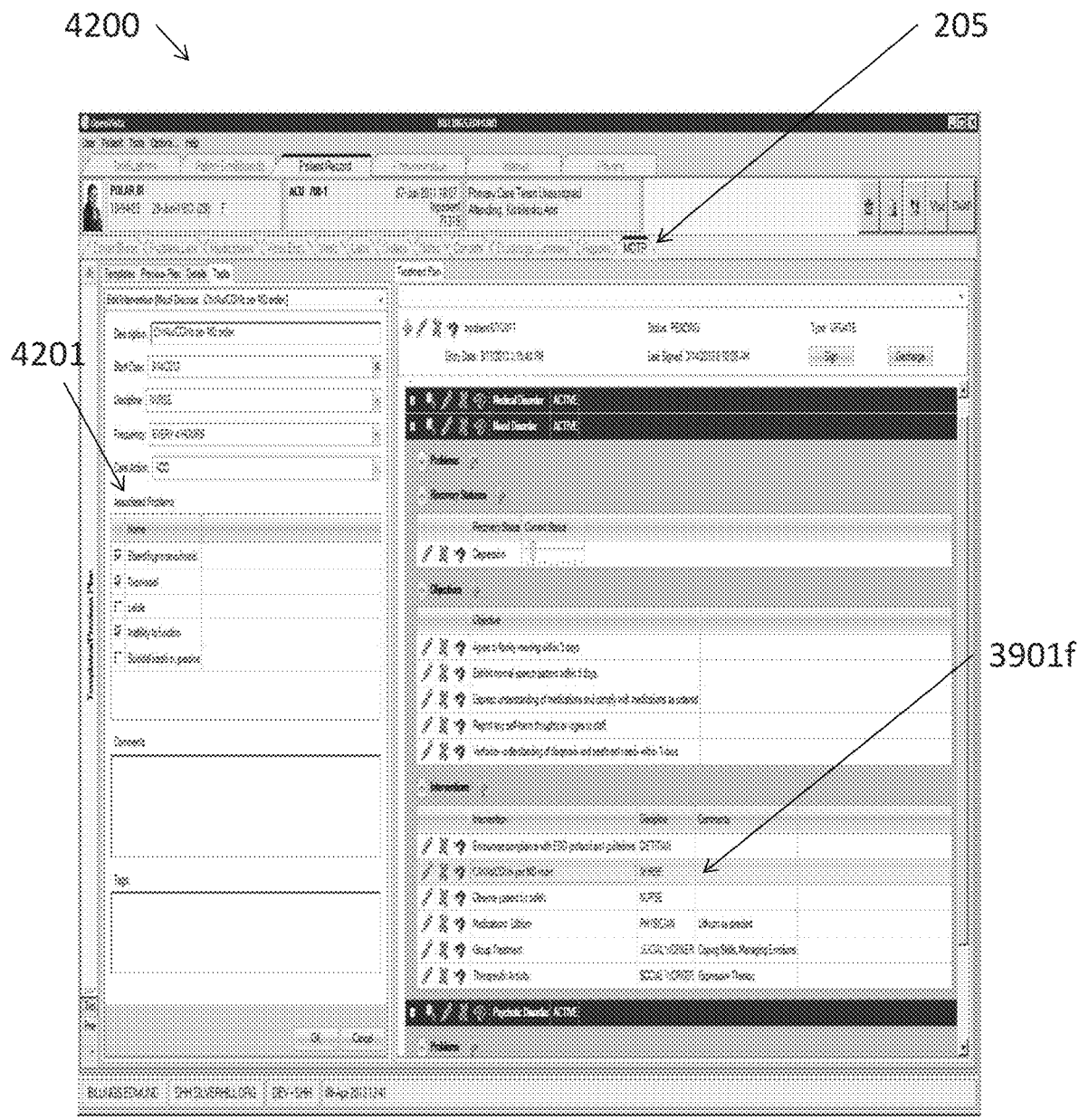
Figure 43:
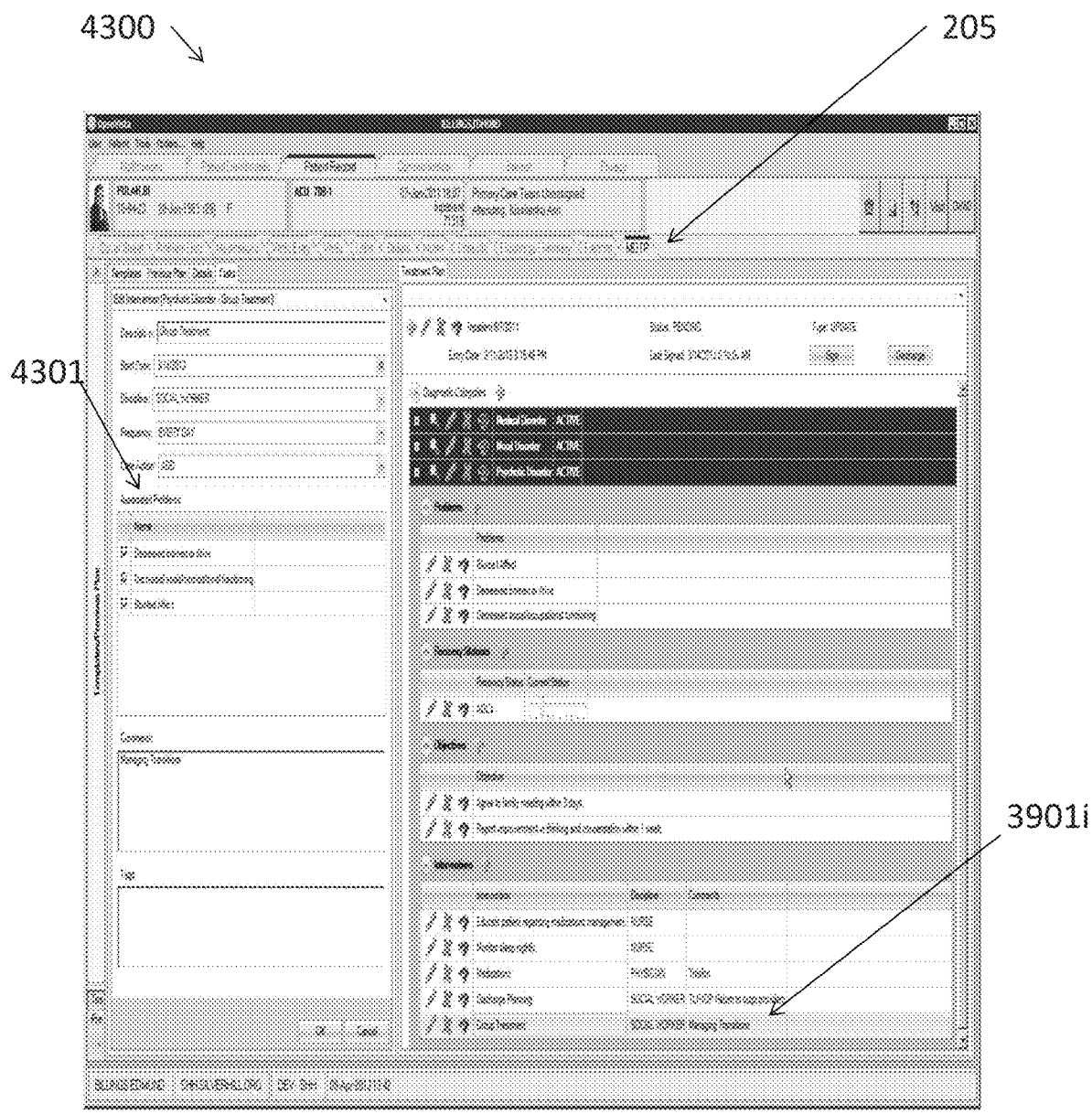

Team members can collaborate to form the comprehensive plan in a variety of ways. As shown in FIG. 39, in a step 3900, the team can decide to have a recovery status of improved body image for an axis 2 medical disorder. The team can set a set of shared objectives and interventions 3901 in the MDTP pane 205. As an example, the nurse can enter two interventions 3901a, 3901b, the psychiatrist can enter one intervention 3901c, and the social worker can enter one intervention 3901d. As shown in FIG. 40, in a step 4000, the team can decide to care for 5 different problems 235a, 235b, 235c, 235d, and 235e for an axis 1 mood disorder. The team can set a recovery status scale 3701 of the depression and can set a set of shared objectives 245a, 245b, 245c, 245d, and 245e. As shown in FIG. 41, each team member can entire their interventions 3901e, 3901f, 3901g, 3901h, 3901i, and 3901j. This entering of the interventions can be done during a collaborative discussion on the care of the patient. Comments are entered to specify interventions and clarify care to be given. The interventions can be associated with multiple problems. As shown in FIGS. 42 and 43, in steps 4200 and 4300, specific interventions, e.g., the intervention 3901f in FIG. 42 and the intervention 3901i in FIG. 43, can be associated to one or more of the problems, e.g., problems 4201 in FIG. 42 and problems 4301 in FIG. 43. This can allow matrixing and eliminate the redundancy experienced with most treatment planning applications, making it simpler to document progress on the interventions.

Figure 44:
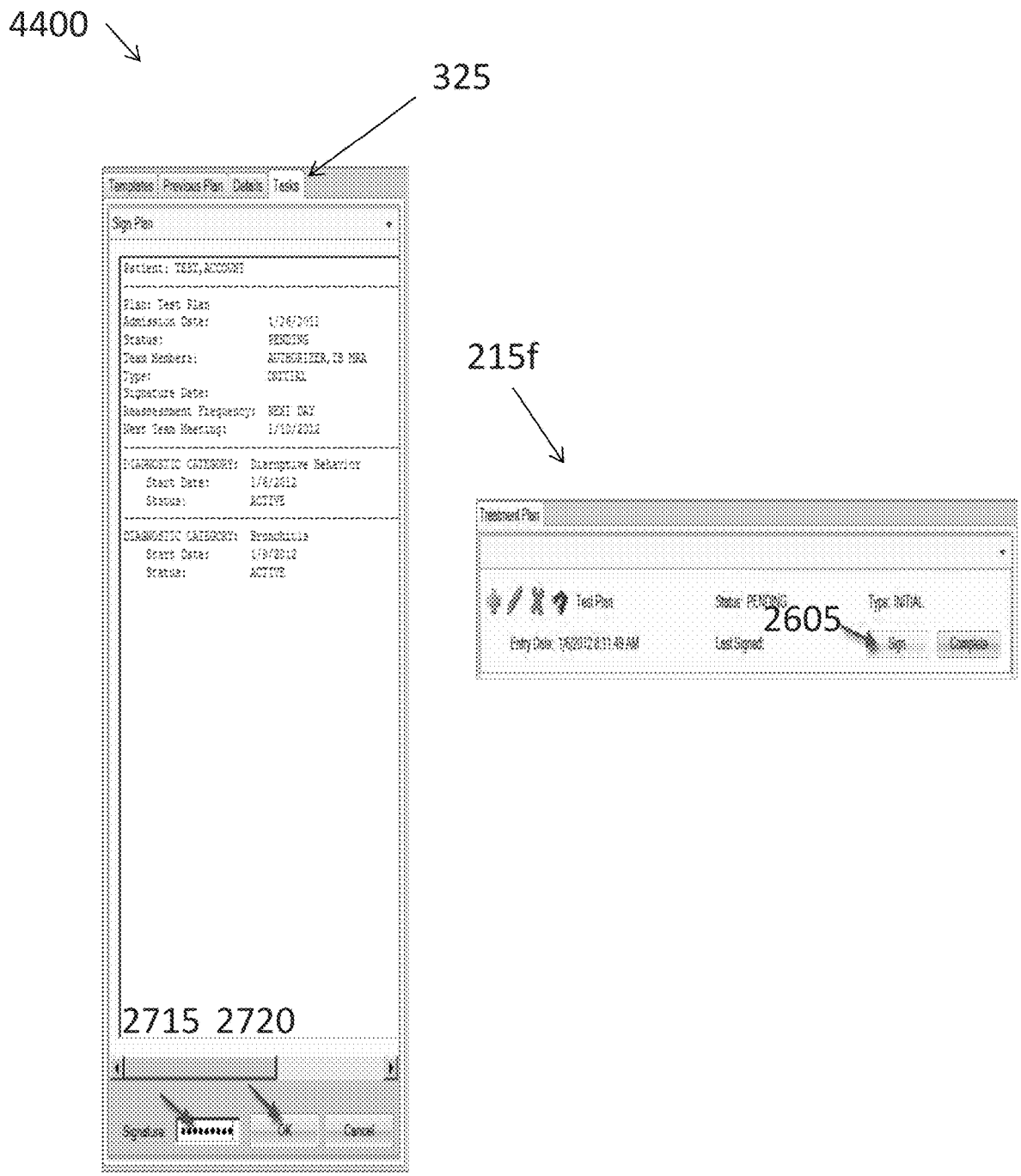
Figure 45:
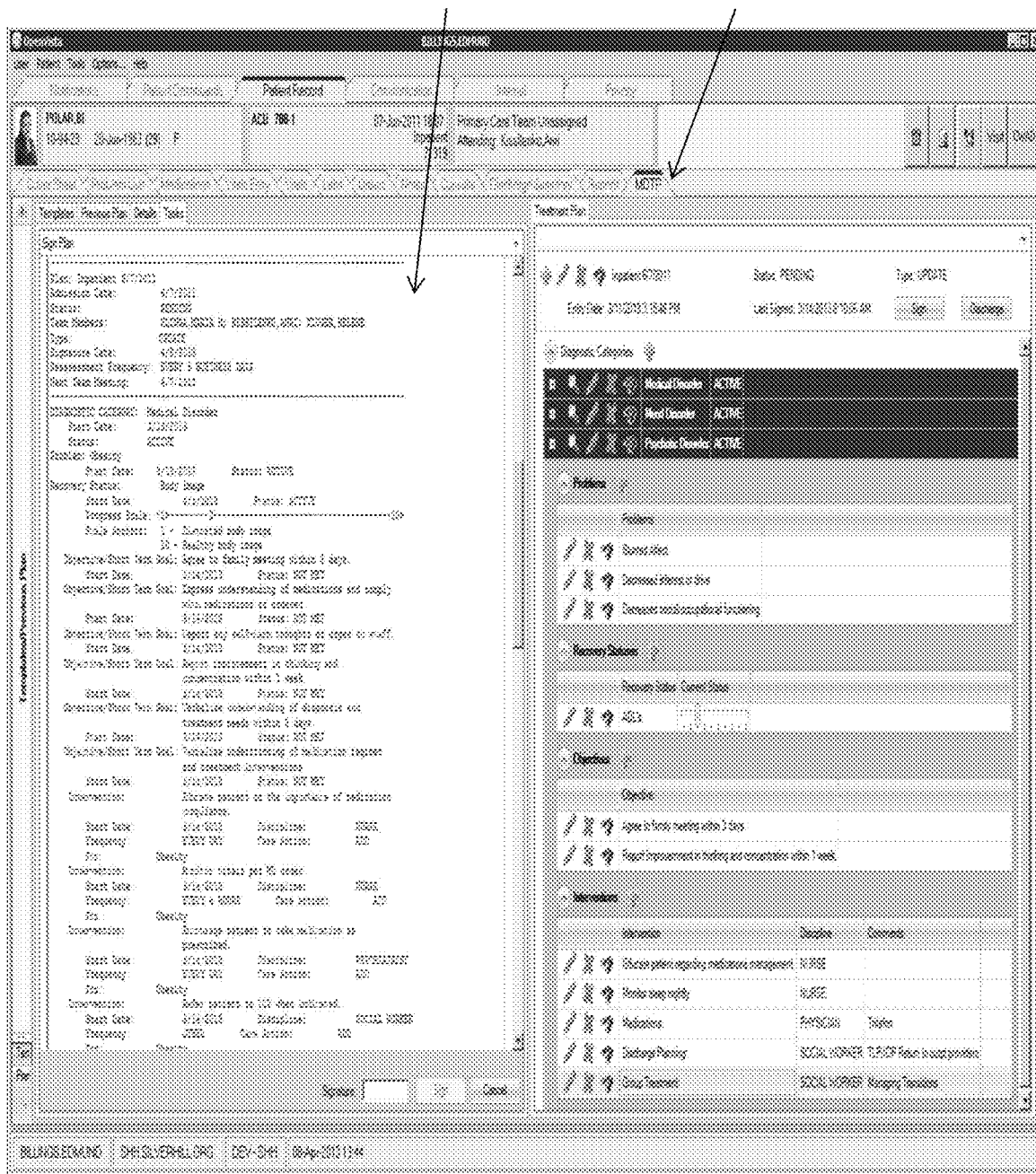
Figure 46:
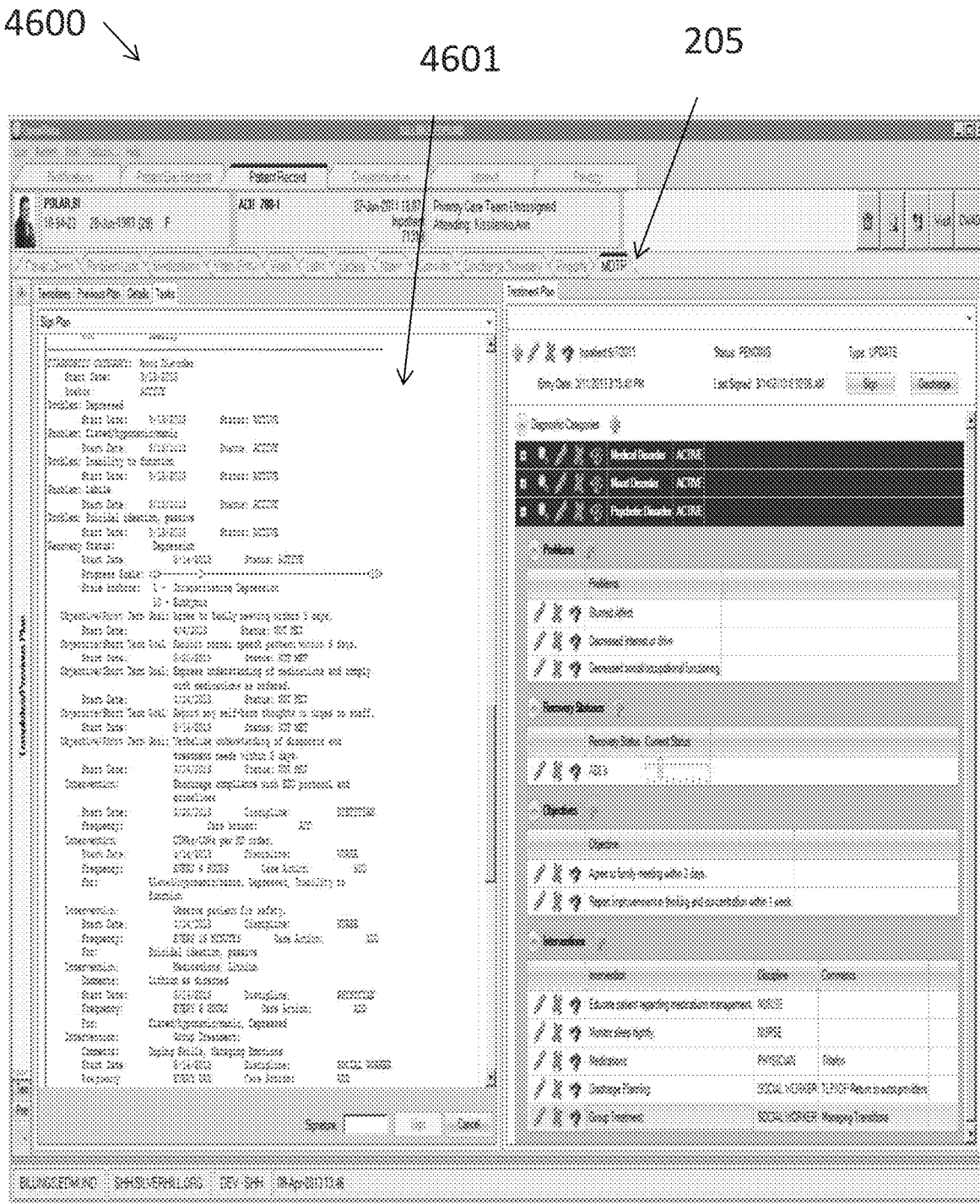

Once the comprehensive MDTP plan is formed, it can be reviewed for signature in a step 4400 as shown in FIG. 44. A team member can enter his or her signature in the signature box 2715 and click the OK button 2720 to enter the signature before electronically signing with the signature with sign button 2605 in treatment plan pane portion 215f. In a step 4500 shown in FIG. 45, the treatment plan is signed and documented as a note 4501 into the tasks tab 225. The current active plan is always reviewable at the MDTP tab 205. The current MDTP is always "on the chart" while all changes are documented as notes. In a step 4600 shown in FIG. 46, the treatment plan note 4501 lists specific interventions with the multi-disciplinary provider noted. These interventions will be available for the team member to pull into their progress notes where they can document the patient's progress on each.

Figure 47:
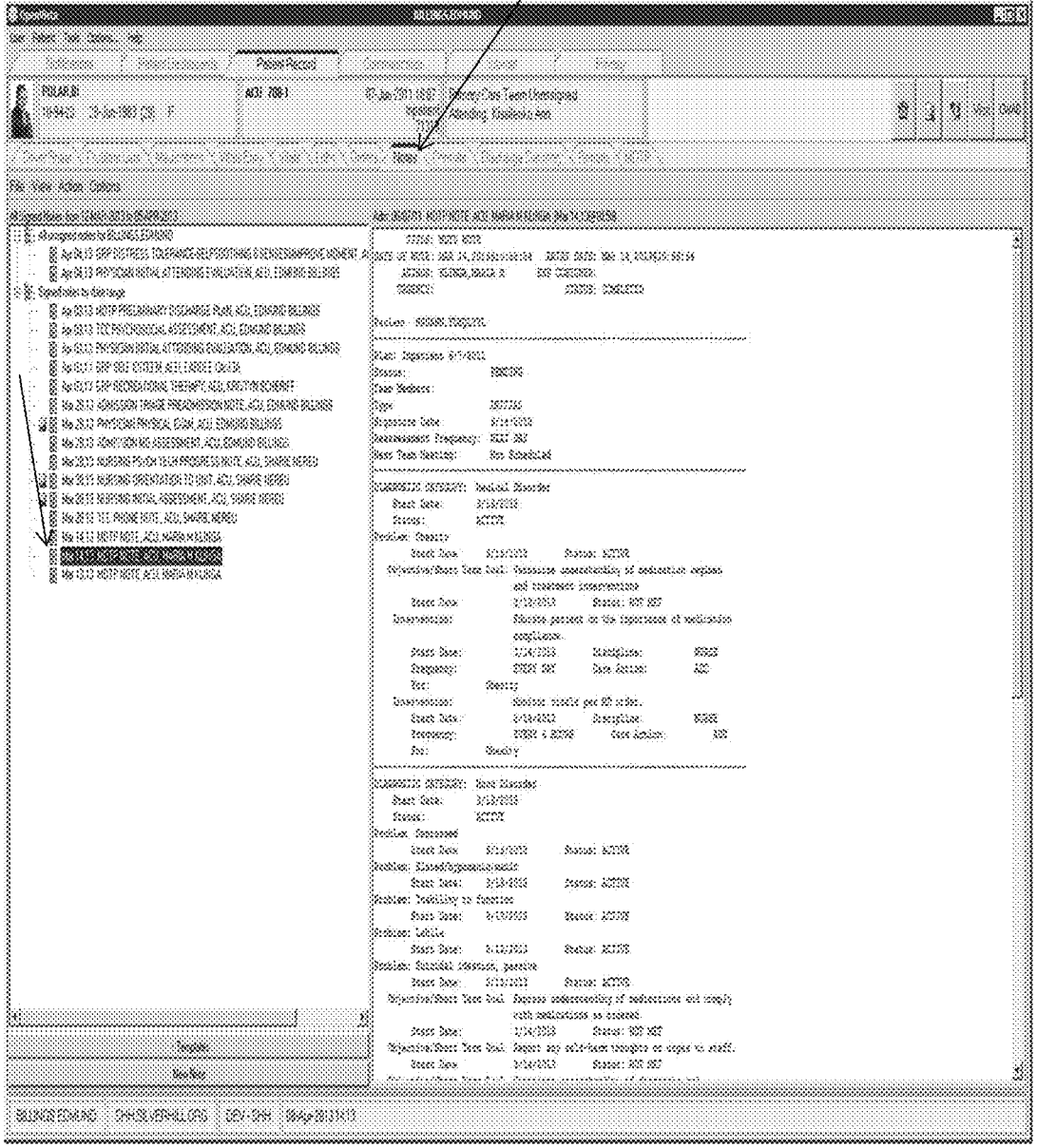
Figure 48:
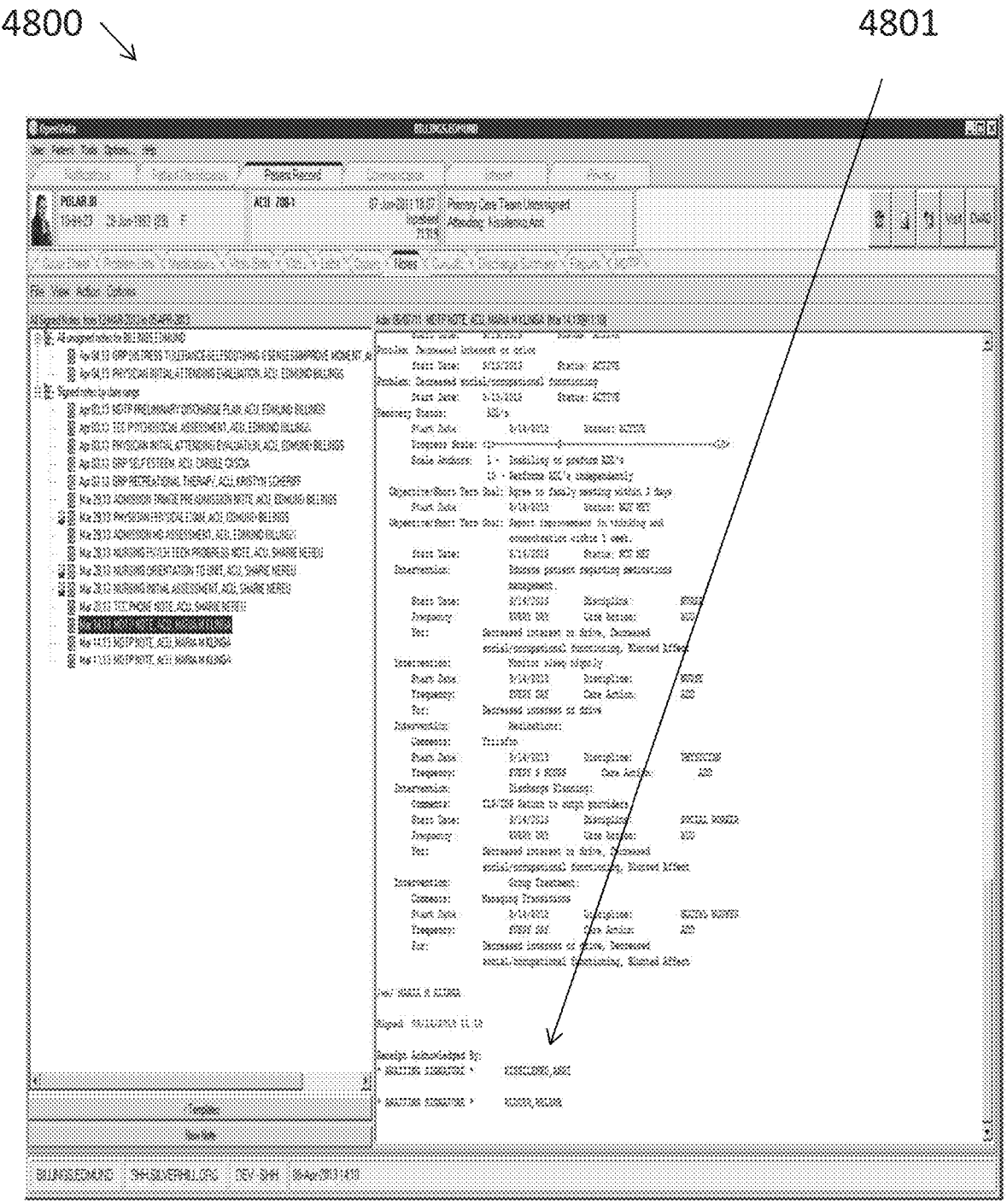
Figure 49:
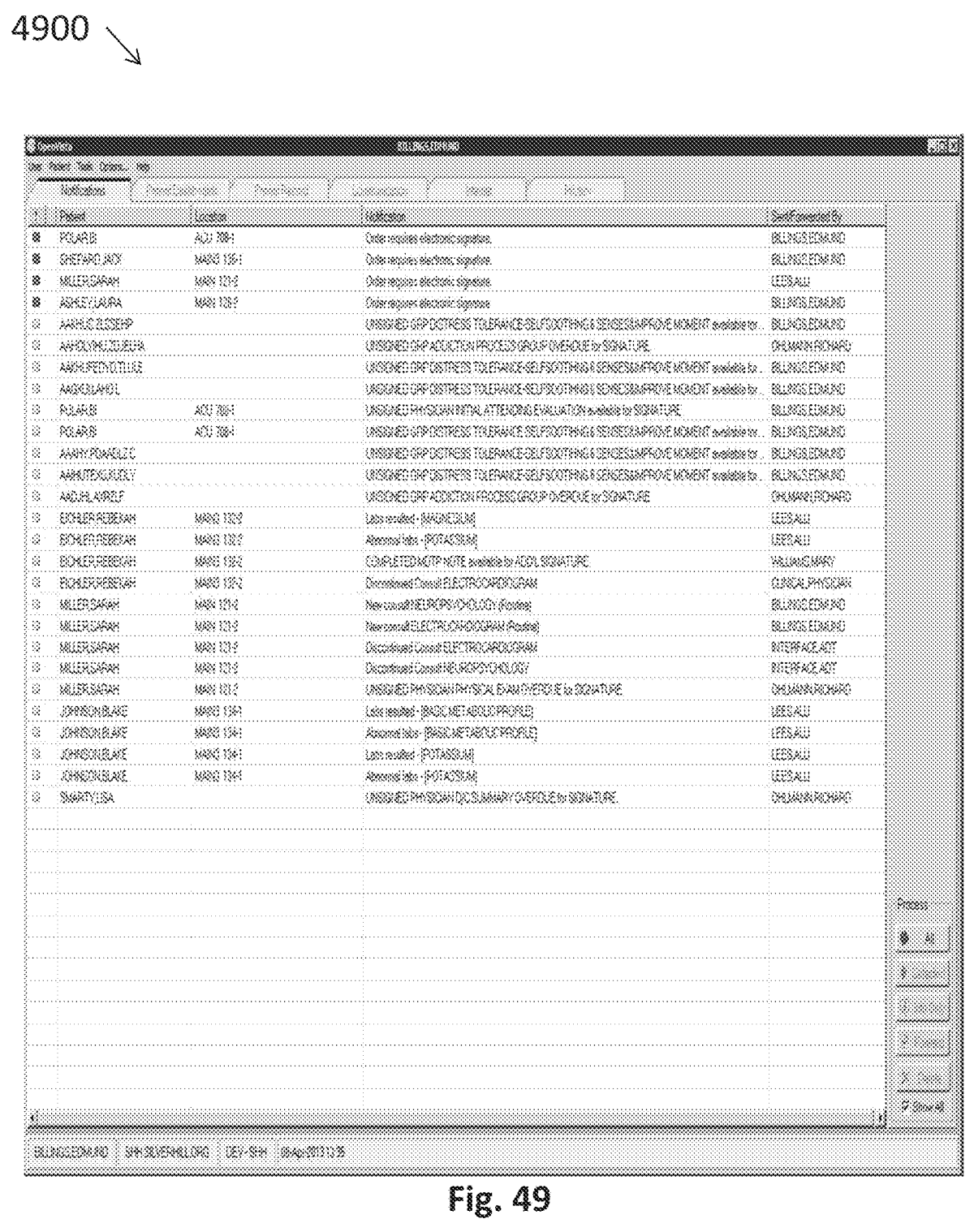

When the MDTP note 4501 is signed, it is time date stamped and placed in the notes tab 4701 as part of the record of care in a step 4700 shown by FIG. 47. As shown by FIG. 48, in a step 4800, the organization can configure signature and co-signature 4801 so that the team is on a collaborative plan. Signatures can be assured through notification. As shown by FIG. 49, in a step 4900, the MDTP routinely notifies the team before the patient is discharged. The team can be notified to place a comprehensive treatment plan on the chart within 24 hours and update the treatment plan every 72 hours for example.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method executed on a computing device to reduce redundant interventions during the generation and implementation of a collaborative medical treatment plan on a patient, the method comprising:
   receiving a plurality of selected diagnostic categories and a list of selected team members from a computing device in communication with a treatment plan server;
   generating an initial treatment plan stored on the treatment plan server based on the selected diagnostic categories;
   permitting client devices associated to the selected team members collaborating virtually to access the initial treatment plan on the treatment plan server, wherein the client devices are heterogeneous and networked;
   updating the treatment plan periodically on the treatment plan server for access by the selected team members, wherein updating the treatment plan comprises:
   (i) receiving a plurality of treatment objectives and a plurality of interventions based on the initial treatment plan from the client devices, each treatment objective being associated to one or more interventions; and
   (ii) generating a completed treatment plan by:
   (1) associating each individual team member to one or more interventions,
   (2) generating a matrix of the individual team members and their associated one or more interventions, and
   (3) assigning the interventions to the team members based on the matrix such that one or more individual interventions assigned to a single team member is shared between multiple treatment objectives; and
   directing the plurality of client devices to present the updated treatment plan to the selected team members through the native user interfaces of the client devices, wherein said graphical user interfaces for the updated treatment plan are individualized for each selected team member.

2. The method of claim 1, wherein updating the treatment plan comprises updating the completed treatment plan as the plurality of interventions are undertaken by the plurality of team members.

3. The method of claim 1, wherein updating the treatment plan comprises receiving one or more progress reports on the treatment objectives from the client devices.

4. The method of claim 3, wherein updating the treatment plan comprises collating the one or more progress reports and updating the completed treatment plan based on the collated one or more progress reports.

5. The method of claim 1, wherein receiving the plurality of treatment objectives and the plurality of interventions from the client devices comprises providing a user interface for the client devices to one or more of enter or select one or more of the plurality of treatment objectives or the plurality of interventions.

6. The method of claim 5, wherein the user interface comprises a generalized treatment planning section comprising a pre-determined list of patient diagnostic categories or problems selectable to form one or more of the treatment objectives, the one or more of the treatment objectives being patient specific.

7. The method of claim 6, wherein the user interface comprises a patient-specific planning section, and wherein the one or more of the treatment objectives are formed by dragging a visually perceptible element representative of a patient diagnostic category or problem from the generalized treatment planning section to the patient-specific planning section.

8. The method of claim 6, wherein the generalized treatment planning section comprises a plurality of interactive tabs, the plurality of interactive tabs comprising one or more of a templates tab for creating patient data entries, a previous plan tab for displaying a prior course of patient treatment, a details tab for displaying patient-specific data, and a task tab for adding or editing patient-specific tasks.

9. The method of claim 8, wherein the tasks tab comprises entries for one or more of a patient problem description, a reassessment frequency, a patient problem type, an entry for an appropriate healthcare or medical professional team member, one or more comments, or one or more tags.

10. The method of claim 1, wherein updating the treatment plan periodically comprises instructing one or more of the client devices to provide one or more of an audio or visual notification to the team member associated to said one or more of the client devices to provide updates to the treatment plan.

11. The method of claim 10, wherein the one or more of an audio notification or a visual notification are provided according to a timing interval selected by one or more of the selected team members or the admitting medical professional.

* * * * *